(12) United States Patent
Boscherini et al.

(10) Patent No.: US 12,357,248 B2
(45) Date of Patent: Jul. 15, 2025

(54) SURGICAL TABLE WITH AN INTEGRATED IMAGING DEVICE

(71) Applicants: Duccio Boscherini, Pully (CH); Serge Rovenne, Vevey (CH)

(72) Inventors: Duccio Boscherini, Pully (CH); Serge Rovenne, Vevey (CH)

(*) Notice: Subject to any disclaimer, the term of this patent is extended or adjusted under 35 U.S.C. 154(b) by 574 days.

(21) Appl. No.: 17/435,828

(22) PCT Filed: Feb. 27, 2020

(86) PCT No.: PCT/EP2020/055148
§ 371 (c)(1),
(2) Date: Sep. 2, 2021

(87) PCT Pub. No.: WO2020/178136
PCT Pub. Date: Sep. 10, 2020

(65) Prior Publication Data
US 2022/0151574 A1  May 19, 2022

(30) Foreign Application Priority Data
Mar. 4, 2019 (EP) .................................. 19160439

(51) Int. Cl.
*A61B 6/04* (2006.01)
*A61B 6/40* (2024.01)
*A61B 6/42* (2024.01)

(52) U.S. Cl.
CPC .......... *A61B 6/0407* (2013.01); *A61B 6/4007* (2013.01); *A61B 6/4266* (2013.01)

(58) Field of Classification Search
CPC .... A61B 6/0407; A61B 6/4007; A61B 6/4266
See application file for complete search history.

(56) References Cited

U.S. PATENT DOCUMENTS

| | | | | |
|---|---|---|---|---|
| 3,549,885 A | * | 12/1970 | Andersson | A61B 6/022 378/197 |
| 5,515,416 A | * | 5/1996 | Siczek | A61B 6/4441 378/197 |
| RE38,560 E | * | 8/2004 | Hug | G01T 1/166 250/363.08 |
| 7,640,607 B2 | * | 1/2010 | Guertin | A61B 6/4441 5/601 |
| 8,859,974 B2 | * | 10/2014 | Tsukerman | A61B 6/037 250/363.05 |
| 2005/0054915 A1 | | 3/2005 | Sukovic et al. | |
| 2005/0135550 A1 | * | 6/2005 | Man | A61B 6/4014 378/4 |

(Continued)

*Primary Examiner* — Myles A Throop
(74) *Attorney, Agent, or Firm* — Klarquist Sparkman, LLP

(57) ABSTRACT

A surgical table with an integrated imaging device can obtain images of a patient's body part. The surgical table can include a base, a patient support platform, at least one platform support connected to the base, and an imaging device support that is mounted on the base and an imaging device mounted on the imaging device support. The patient support platform can be at least partially positioned between a first arm and a second arm. A first radiation source can be positioned in or on the first arm and a first radiation detector can be positioned in or on the second arm, with the first radiation detector arranged to detect at least a portion of the radiation emitted by the first radiation source.

18 Claims, 12 Drawing Sheets

(56) References Cited

U.S. PATENT DOCUMENTS

| | | | |
|---|---|---|---|
| 2005/0226363 A1* | 10/2005 | Edie | A61B 6/4275 |
| | | | 378/9 |
| 2007/0183587 A1 | 8/2007 | Baumann et al. | |
| 2008/0123804 A1* | 5/2008 | De Man | A61B 6/032 |
| | | | 378/9 |
| 2009/0022278 A1* | 1/2009 | Hugg | A61B 6/06 |
| | | | 378/149 |
| 2011/0228899 A1* | 9/2011 | Funk | A61B 6/542 |
| | | | 378/9 |
| 2012/0198625 A1 | 8/2012 | Jackson | |
| 2013/0343509 A1* | 12/2013 | Gregerson | A61B 6/4014 |
| | | | 378/62 |
| 2015/0131775 A1* | 5/2015 | Yorkston | A61B 6/4405 |
| | | | 378/17 |
| 2016/0158082 A1* | 6/2016 | Gainor | A61G 13/107 |
| | | | 5/690 |
| 2017/0020465 A1 | 1/2017 | Friebe | |
| 2017/0164910 A1* | 6/2017 | Cao | A61B 6/4275 |
| 2018/0214333 A1* | 8/2018 | McKenney | A61H 1/0222 |
| 2018/0289339 A1* | 10/2018 | Fortuna | A61B 6/4241 |
| 2022/0151574 A1* | 5/2022 | Boscherini | A61B 6/4007 |

\* cited by examiner

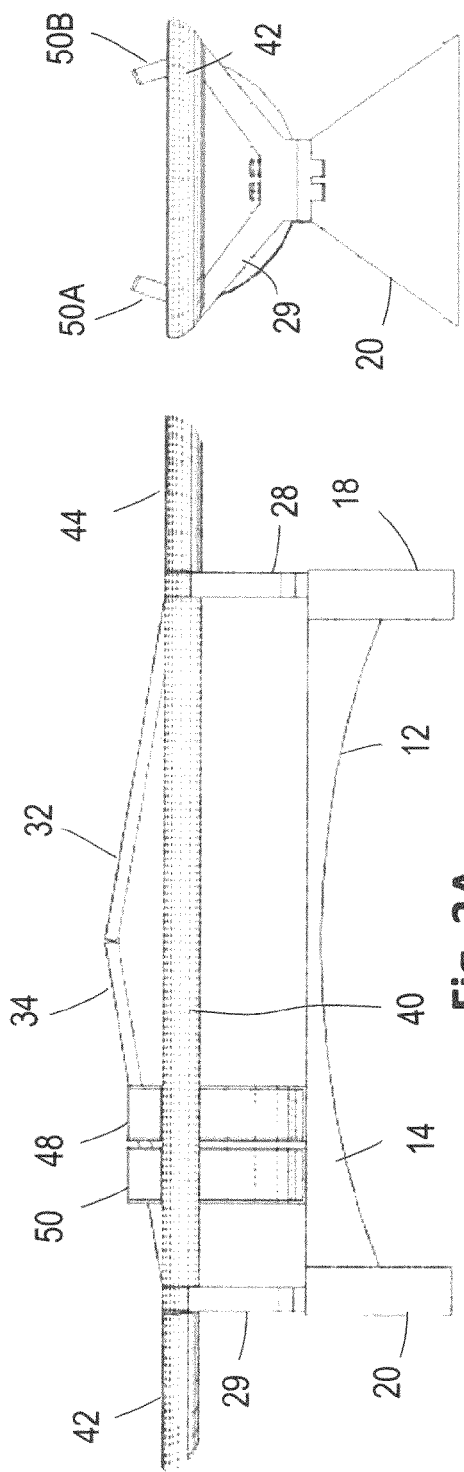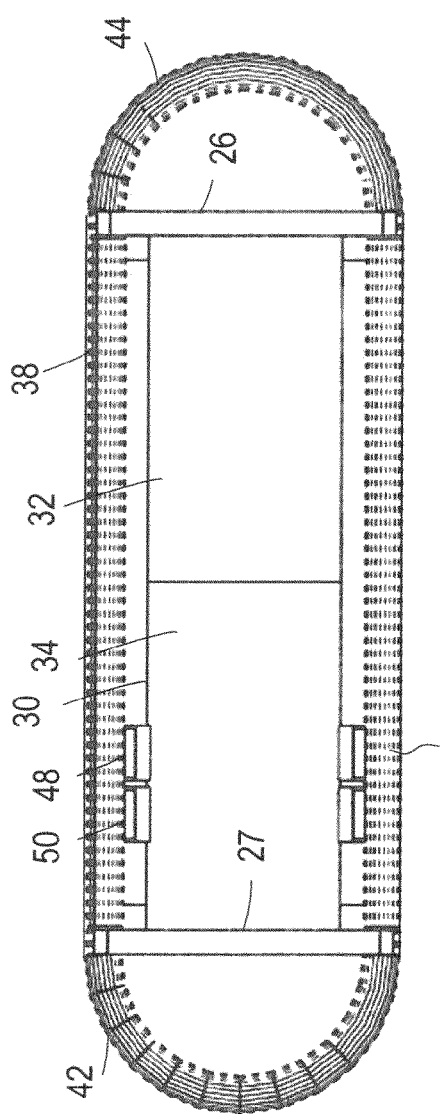

SURGICAL TABLE WITH AN INTEGRATED IMAGING DEVICE

CROSS REFERENCE TO RELATED APPLICATIONS

This is the U.S. National Stage of International Application No. PCT/EP2020/055148, filed Feb. 27, 2020, which was published in English under PCT Article 21 (2), which in turn claims the benefit of European Patent Application No. 19 160 439.6, filed Mar. 4, 2019. The prior applications are incorporated herein by reference in their entirety.

DESCRIPTION

The present invention relates to a surgical table with an integrated imaging device.

There have been different approaches to 3D interoperative imaging device technology to provide assistance and/or navigating during surgery employing imaging devices external to the surgical table. To perform image acquisition, either the surgical table is moved to the imaging device (for example by a robotic arm) or the imaging device is moved to the surgical table. An example of such external imaging device is disclosed e.g. in U.S. Pat. No. 7,188,998 B2 or US 2012/0330134 A1 which is a mobile imaging device equipped with an RX tube and a flat screen detector. The closed ring arm can be opened in a C-form to allow the positioning of the moveable imaging device with respect to the surgical table. When positioned, the device performs a rotational scan to acquire a two-dimensional or three-dimensional image of the relevant part of the patient's body.

Known imaging devices have a number of disadvantages. They are generally bulky and heavy. Since they impede the access to the patient, they often need to be removed from the operating field and be repositioned during surgery. Every time the imaging device is repositioned with respect to the surgical table, a time consuming calibration of the imaging device needs to be performed. This results in increased surgical time and radiation dosage and reduced accuracy. Further, conventional external imaging devices (for example employing closed ring arm construction) restrain the surgeon ergonomics and generate sterility violation risks.

The present invention aims at alleviating or avoiding at least some of the above problems.

According to an aspect there is provided a surgical table with an integrated imaging device comprising
a base configured to be placed on the floor of an operating room and optionally to be fixed to the floor;
a patient support platform configured to support at least a portion of the patient's body that is placeable on an upper surface of the patient support platform;
at least one platform support connected to the base and configured to support the patient support platform on the base;
a imaging device support that is mounted on the base; an imaging device mounted on or respective connected to the imaging device support, said imaging device including
at least one imaging unit comprising a first arm (first jaw) and a second arm (second jaw), wherein the patient support platform at least partially is arranged between the first and the second arm; and
a first radiation source positioned in or on the first arm and a first radiation detector positioned in or on the second arm, said first radiation detector arranged such as to detect at least a portion of the radiation emitted by the first radiation source.

Since the imaging device is mounted on or in other words connected to the base via the imaging device support, it forms an integral part of the surgical table itself. Thus, the relative position of the imaging device support and of the imaging device with respect to the surgical table is preferably precisely known or is determinable in a precise manner, which improves the precision of the image acquisition and facilitates the calibration of the imaging device. Due to the improved precision and reduced calibration time the patient exposure time and the radiation dosage may be reduced and the security of the surgical intervention may be improved. Further, since the access to the patient is also facilitated, the overall surgical time and the associated risks may be reduced. Still further, the risk of sterility violation by employing an external imaging device may be reduced. Still further, since the imaging device is an integral part of the surgical table and is directly suspended from the surgical table, it is possible to achieve a considerable space economy. Further, no additional, as a rule rather bulky base for supporting the external imaging device occupies floor space and obstructs the surgeon and the supporting staff. Other advantages include smart imaging integration enabling ALARA (As Low As Reasonably Achievable) dose for staff and patient, enhanced manoeuvrability, weight reduction, simultaneous registered imaging of pre and per operating, etc.

The imaging device may be mounted on or connected (e.g. fixed) to an imaging device support, for example in form of a ring or a V-structure, thereby realizing a specific geometry to collect a series of projection views. The imaging device support is mounted on the surgical table and can be preferably translated longitudinally along the surgical table (such as a carbon surgical table) to preferably image all patient areas in one or several separate temporal acquisitions.

The imaging device support may be for example slidably mounted on the base, thus facilitating the access to the patient and/or allowing images of different parts of the patient to be taken. For example, the base may comprise a sliding rail or track that extends along a longitudinal axis of the base (and the surgical table), on which the imaging device support is slidably mounted. Any other type of connection that enables sliding movement of the imaging device support may be employed. This facilitates the access to the patient during surgery and the image acquisition of different parts of the patient's body.

The at least two arms of the imaging unit may be arranged at the two sides of the patient support platform in a transverse direction of the patient support platform (i.e. direction orthogonal to the longitudinal direction of the patient support platform and the surgical table). In other words, the patient support platform is at least partially positioned between the at least two arms of the imaging unit. When performing imaging, the imaged part of the patient's body positioned on the upper surface of the patient support platform is thus between the radiation source and the radiation detector, so that radiation emitted from the radiation source may propagate through the imaged part of the patient's body and be detected by the radiation detector. The at least one imaging unit may be rotatable (for example around 360 degrees or less) with respect to the base and/or the patient support platform and more specifically with respect to a longitudinal axis of the surgical table, thus allowing images of the patient to be taken from multiple directions. To this extent the at least one imaging unit may be rotatably mounted on or connected to the imaging device support.

The at least one imaging unit may also be tiltable or pivotable with respect to the base and/or the patient support platform and more specifically with respect to an axis that is orthogonal to the longitudinal axis of the surgical table. This may further facilitate the access to the patient and allow images of the patient to be taken from different directions.

The surgical table may further comprise at least one actuator (e.g. a linear actuator) for moving the imaging device support with respect to the base and/or for rotatably and/or pivotably moving the at least one imaging unit. The actuator or at least parts of the actuator (such as electrical cabling and/or other electrical components, motors, etc.) may be housed in the base and/or other components of the surgical table. This considerably reduces the risk of sterility violation and facilitates maintaining sterility condition throughout the surgery procedure.

The arms of the at least one imaging unit may be arranged so as to jointly substantially have a c-form, a v-form or any other suitable form. This enables open and easy access to the surgical field.

It is possible to arrange a plurality of radiation sources and detectors within one imaging unit. The plurality of radiation sources and detectors may be arranged in an alternating pattern. For example, the second arm may include a second radiation source and the first arm may include a second radiation detector arranged such as to detect at least a portion of the radiation emitted from the second radiation source. Further, it is possible to employ a plurality of imaging units, wherein one arm of each imaging unit be provided with a radiation source and the other arm of the imaging unit may be provided with a radiation detector arranged to detect at least a portion of the radiation emitted from the respective radiation source. In an example, the radiation sources and detectors provided on the individual imaging units may be arranged in an alternating manner, so that for example the radiation source of one imaging unit is adjacent to a radiation detector of another imaging unit.

The radiation source and/or the radiation detector may have an array structure (for example a one- or two-dimensional array structure) comprising a plurality of radiation or detector elements, respectively. The plurality of radiation and detector elements may be arranged on the surface of the first and the second arm, respectively, which faces the patient platform support.

The plurality imaging units may be independently movable with respect to the base and/or the patient support platform. For example, each imaging unit may be independently rotatable around the longitudinal axis of the surgical table. Further, the imaging units may be movable with respect to each other, for example may be tiltable with respect to each other and/or with respect to the base and/or the patient support platform.

The imaging device may be any suitable imaging device, for example a radiographic imaging device, a magnetic resonance imaging device, a positron emission imaging device, an ultrasound imaging device, a computer tomography imaging device, etc. Different or the same types of imaging devices may be provided on a plurality of imaging units. As described above, the imaging device may work on the principle of a rotating scan. Initially, the at least one imaging unit may be in a retracted (rest) position, allowing the surgical team unimpeded access to the patient. During image acquisition, the at least one imaging unit may be rotated around the patient, thus enabling capturing of images from different directions. The signal captured by the at least one radiation sensor of the imaging unit may be transmitted to a suitable processor to obtain an image of the patient's body or a part thereof, for example a two-dimensional or a three-dimensional image.

The type of the imaging device employed is not specifically limited. The imaging device may be any intraoperative imaging modality that supports a surgeon in identifying vital structures and discriminating the structures, preferably in real-time. The real-time imaging capability is not only especially important for spinal procedures where the surgeon lacks tactile and visual information, but also to other interventional or diagnostic procedures involving surgeons, radiologists, orthopaedists etc. The imaging device may be a 2D or 3D imaging device. 3D imaging devices provide high-resolution images, can visualize region(s) of interest (e.g. pedicle in spine typical) in HR, and can be operative-specific due to targeted on location acquisition and/or pre-operative imaging planned (scout view). The imaging device may be for example any type of CT (Computer Tomography) imaging device or system developed for image-guided surgery or any medical image-guided procedure (e.g. interventional radiology, angio etc).

As described above, the imaging device is mounted on or connected to (e.g. fixed) to a support structure (imaging device support), thereby realizing a specific imaging geometry that preferably enables collecting a series of projection views. For example, an electron emitter (cathode) for an X-ray source and a flat panel detector (ConeBeamComputedTomography) or a linear detector (ComputedTomography) of an exemplary imaging device may be connected (e.g. fixed) to a ring or a V-structure (exemplary imaging device support), thus realizing an imaging geometry, that preferably enables collecting a series of projection views. The imaging device support is mounted on the surgical table (such that it forms an integral part of the surgical table) and can be preferably translated longitudinally along the surgical table (such as a carbon surgical table) to image all patient areas in one or several separate temporal acquisitions.

Preferably, the geometry or respectively arrangement of the imaging device and its support enables performing repetitive imaging steps involving image recording (e.g. CBCT or CT) to capture 3D information for large field of view of human imaging. For example, any geometry with the following functions and/or features may be employed:
(i) either swinging the imaging device (radiation) source (e.g. a X-ray source (cathode)) through the space;
(ii) or using an array of fixed and distributed low power miniaturized cathode sources (stationary geometry) in conjunction with an array of fixed and distributed small detectors or large flat panel detector(s). Such a geometry using fixed and distributed cathodes enables miniaturization, since every cathode has low power consumption and no more mechanical swinging support is need. Further, such geometry exhibits higher resolution by blur reduction due to the lack of mechanical swinging and calorific reduction as the consumption is low.

Regarding option (i), alternative geometries are possible. For example, there are several ways to design a system capable of acquiring a set of images from a set of limited angles. This could be done is a way that is minimally invasive to the surgeon but might not result in a fully 3D data set. Accordingly, the resultant reconstruction might only allow viewing of the subject from one of the angles in the set used to acquire the data. In another alternative, a system could be employed to have two sets of angles to collect sagittal and coronal planes of reconstruction allowing views of the spine from the top and the side. This method was explored in the early 2000s and was called XBeam. It would require two sets of strip detectors illuminated by a collimated beam such that each strip detector when moved would collect a particular angular projection of the subject.

The image detector may comprise at least one radiation source and at least one radiation detector. Any radiation source, the performance of which can be controlled, for example by voltage and/or current manipulation can be employed. Further, any detector enabling specific spectrum recording can be employed. Performance control and multiple spectrum recording can be used for Dual Energy or Spectral Energy imaging that can provide additional tissue information, such as the effective atomic number, to improve material discrimination, dose calculation and different quantitative estimation for various clinical applications.

Generally, when scanning an object, the measured Hounsfiled Unit [HU=CT number] in a voxel is related to its linear attenuation coefficient that depends both on the mass density and the elemental composition of the scanned object, similar HU can be measured at a certain photon energy for different materials and, as a consequence, cannot be distinguished in a CT scan. However, by exploiting the differences of X-ray attenuation coefficients of tissues at different energies, materials can be distinguished when recording the attenuation at different energies or beam spectra (Dual Energy or Spectral Energy Imaging). In this approach, a CT scanner is capable of distinguishing between materials having different atomic number (e.g. calcium and iodine) when scanning an object at two different beam spectra (e.g. 100 kV and 140 kV). The basic principle of dual-energy imaging is based on acquiring two datasets from the same anatomical area, for example with different X-ray voltages, or with one voltage but recording different portions of the spectrum or different energy windows. There are two main approaches: projection-based or pre-processing methods or image-based or post-processing methods.

The imaging device may for example be a CT scanner. A CT scanner typically comprises an X-ray source and one or more detector(s), arranged in a specific geometry. The X-ray source is typically capable of emitting energies between several kV (e.g. 40 kV and 120 kV) at one or several focal spot sizes (e.g. 0.3 mm and 0.6 mm) with one or multiple several tube currents (e.g. comprised between 5 mA and 120 mA). The specific parameters of the X-ray source depend on the technology components and/or clinical application goals. The detectors can be classified into two main groups: energy-integrating or energy resolving. The energy-integrating detectors integrate the X-ray signal over time with an energy weighting factor (named detector response) and, therefore, they do not provide energy resolution. These detectors convert X-rays to light via a thin scintillator layer (typically Cesium Iodide or Gadolinium Oxysulfide) and then to charge by an amorphous silicon photodiode (indirect conversion) or directly to charge through a Thin Film Transistor (TFT) array (direct conversion. On the other hand, energy-resolved detectors are capable of distinguishing individual photons coming from a polychromatic spectrum within given energy thresholds. These detectors typically use high speed semiconductors {e.g. Cadmium Telluride (CdTe) or Cadmium Zinc Telluride (CZT) combined with fast readout Application-Specific Integrated Circuit (ASIC)s, with an electronic chain for each pixel of the detector. In other words, with just one X-ray tube voltage acquisition, energy-resolved detectors are capable to record attenuation data from multiple energy bins, whereas with energy-integrating detectors acquisitions with different X-ray tube voltages are necessary to obtain the same kind of information.

Further, any CT imaging geometry modalities capable of acquiring dual-energy data may be employed. For example, the CT imaging may be based on one of the following approaches:

Sequential acquisitions with a conventional CT scanner, dual-source CT systems, twin beam systems and fast-kV switching systems based on energy-integrating detectors;

Dual-layer detectors and photon-counting systems that are based on energy-resolved detectors. In recent years image-based post-processing methods in addition to projection-based DualEnergy CT algorithms have been proposed, to solve or alleviate at least some of the problems of conventional projection-based methods. For example, conventional projection-based methods require an access to dual-energy raw data, which is not accessible in most commercial CT scanners. In addition, low and high energy projections need to be sampled at the same angle or accurately interpolated which is not trivial for dual-source scanners or fast-kV switching systems. With the advent of dual-layer systems and photon-counting detector technology, projection-based methods are becoming more attractive, since the projections from the different energy spectra are obtained without angular separation. Projection-based dual-energy approaches enables improving dose reduction and image quality within the field Image-Guided Surgery. However, the stationary geometry explained previously could also reduce projection-based disadvantages; and Employing energy-resolving photon-counting detectors. Photon-counting detectors count discrete photon interactions according to the associated photon energy. The detector is typically divided into N energy channels or bins, determined by consecutive N+1 energy thresholds, where each one has an independent detector response function (i.e. probability of a photon with energy E to be detected at energy E). Photons detected within one bin are then counted. Photon-counting technology with energy discrimination thresholds opens up the potential transition from dual-energy CT to multi-energy CT or spectral CT imaging, which would allow multi-material segmentation (e.g. tissue characterisation).

For example, the imaging device may be based on any CT imaging solution featuring the following features:

the source and the detector can independently rotate along substantially circular trajectories;

the system is equipped with dynamic X-ray collimation jaws;

the one or several of the source(s) and one or several of the detector(s) can be controlled and activated in conjunction (stationary geometry).

The Field Of View (FOV) of the source and the detector trajectories can be off-centered with respect to the center of rotation of the scanner. In combination or not with synchronized collimation, this allows for large FOV irradiations (i.e. the PA is able to cover the full body outline, also in thorax region including the shoulders) and off-centered acquisitions, which allows reduction of patient dose as unnecessary areas of the patient are not irradiated.

The imaging device may employ any system using energy integrating detector(s), preferably with the possibility to adjust the tube current, the tube voltage and the spectrum filtration at each beam pulse thanks to fast-kilovolt switching capabilities of the source and synchronized filter wheel which allows multi-energy imaging. A filter wheel including openings to place filters (e.g. air, copper, aluminium, copper and silver) may be positioned before the collimator jaws.

The imaging device may employ also any system using energy resolved detector(s), preferably using the possibility to adjust the tube current, the tube voltage and the spectrum filtration at each beam pulse thanks to fast-kilovolt switching capabilities of the source. This allows multi-energy imaging without spectrum filtration.

The at least one platform support may have one end connected to the base (for example fixedly) and a second end configured to support the patient support platform. In an example, two platform supports may be provided at the two opposing ends in the longitudinal direction of the base. Preferably, the at least one platform support is configured to enable altering the vertical height of the patient support platform. Thus, the at least one platform support may comprise a height adjusting mechanism, for example a telescopically expandable and contractable support column and/or an actuator. The height adjusting mechanism may for example be a hydraulic height adjusting mechanism or may employ an electrical motor, for example a linear motor.

The second end of the platform support may be fixedly connected to the patient support platform or may be pivotably connected to the patient support platform, so as to enable pivotal movement of the patient supporting surface or a section thereof with respect to a vertical axis and/or horizontal axis. Thus, the repositioning of the patient may be facilitated. The platform support may further comprise at least one fixing member to fix or secure the patient support platform or a section thereof in a given position, for example a given height position.

In an example, the base comprises a bridge portion provided with a sliding rail or track on its top surface, the sliding rail or track extending in a longitudinal direction. Further, the base may comprise two end struts positioned on both sides of the bridge portion. The two end struts may have a substantially triangular or trapezoidal form, with a lower end being placed on the floor and an upper end being connected to the platform support. The bridge portion and/or the end struts may have a hollow form and may house at least a part of the actuators and/or other moving parts and/or parts of the control mechanism (e.g. a movement control). This considerably reduces the risk of sterility violation and the risk of obstructing the surgical field. Further, under floor lighting may be provided in the bridge portion and/or the end struts to provide a better illumination of the surgical field.

The at least one platform support may also have a substantially triangular or trapezodial form, with the upper broader end being connected to the patient support platform and optionally to a side rail surrounding the patient support platform and the lower, narrower end being connected to the respective end strut of the base.

For example, the at least one platform support may comprise a supporting bar (cross bar) that is connected to the patient support platform and optionally to a side rail surrounding the patient support platform. The connection may be a firm connection or a connection that enables movement of the patient support platform or parts thereof with respect to the supporting bar. The connection may for example be a hinge connection. The at least one platform support may further comprise a V-form or U-form supporting strut having two supporting arms, the upper ends of which are connected to the ends of the supporting bar, respectively. The lower end of the V-form or U-form strut may be connected to the end struts of the base or to an extendable support column.

The surgical table may thus exhibit a triangulated cantilever design that maintains a low centre of gravity and this high stability, while facilitating the access to the patient.

The at least one platform support may be hollow and may house at least a part of electrical cabling, fluid conduits, electrical parts and/or other components, for example of the height adjusting mechanism, thus reducing the risk of sterility violation and/or the obstructing the surgical field.

The patient support platform may be movable in a vertical and/or horizontal direction with respect to the base. For example, the vertical height of the patient support platform may be alterable. As explained above, to the platform support may comprise at least one height adjustment unit or mechanism configured to alter the vertical height of the patient support platform, i.e. the vertical position of the patient support platform with respect to the base. The height adjustment unit or mechanism may for example comprise a support column connectable to the end struts that is extendable in a vertical direction, for example telescopically extendable. The height adjustment unit may further comprise at least one actuator (e.g. a linear motor actuator, a hydraulic actuator, etc.) that causes the vertical movement. For example, the actuator may cause a support column to extend or collapse in a vertical direction. As explained above, the actuators and/or the electrical cabling and/or tubing and/or other components may be housed within the base (for example within the end struts), within the at least one platform support, for example within the support column.

The patient support platform may comprise a plurality of sections that are movable (e.g. pivotable or tiltable) with respect to each other. For example, the patient support platform may comprise a first section and a second section cantilevered off or hinged on the first section. The patient support platform may further comprise a third section cantilevered off or hinged on the second section. Further, at least one section may be movably connected (for example by respective hinges) to the platform support. By the provision of a plurality of sections that are movable with respect to each other it is possible to easily reposition the patient's body when needed during the surgery, for example during a spinal or neurological surgery.

The surgical table may further comprise a side rail (external rail) at least partially surrounding the outer circumference of the patient support platform. The side rail may have for example a U-form, an O-form, a rectangular form or any other appropriate form. In an example, the side rail also surrounds the at least one imaging unit, In other words, the at least one imaging unit may be within the perimeter of the side rail. The side rail thus reduces the risk of interference of the surgeon and the supporting staff with the imaging device. At least a portion of the side rail may be padded with or made of a soft material to prevent injuries of the operating personnel. Further, the side rail may exhibit a cross-sectional form with rounded edges, to prevent injuries.

The side rail may comprise for example two portions on the two long sides of the patient support platform (perimeter portions or perimeter beams) and two curved end rail portions on the short sides of the patient support platform, respectively. The opposing ends of the supporting bar of the platform support may be connected to the side rail. The perimeter portions may be substantially straight or slightly curved and the end rail portions may be semi-circular or semi-oval. Other forms are also possible.

The side rail may be provided with one or more mounting portions connectable to respective mounting portions of additional external devices, such as for example monitor, touchscreen, etc. For example, the at least one mounting portion may be provided on the curved end rail portion. The at least one mounting portion may for example comprise a mounting leg on which a mounting arm of a monitor stand is mountable. Any other type of connectors may be employed.

The side rail may be further provided with an instrument placement portion on or in which surgical equipment and accessories may be mounted or placed. For example, the perimeter rail portions (perimeter beams) may be extruded profiles that act as a conduit and a mounting track (instrument placement portion) for accessories and equipment.

Still further, the side rail or a part thereof (for example one of the perimeter portions and/or one of the end rail portions) may have a hollow form. Various components, such as electrical cabling, fluid conduits, electrical components (e.g. of the height adjustment control mechanism) and/or other components may be provided within the side rail of a part thereof. In other words, the side rail or a part thereof may house any of the above mentioned components. This considerably improves the maintenance of sterility of the surgical table and reduces the risk of obstructions of surgical field.

The side rail may also be provided with a control interface, for example for a control interface for the control of the height adjustment mechanism (for increasing or decreasing the height of the patient support platform) and/or a control interface for positioning of the imaging device (e.g. moving the imaging device forward or backward, to a specific position, such as initial or retracted position, memorized position, etc.). The control interface may comprise buttons, a touch screen or any other suitable human-machine interface elements.

The surgical table may further comprise a tracking system (e.g. optical, electronical, etc. tracking system) for tracking the position of the imaging device support and/or the imaging device with respect to the base and/or the patient support platform. In an example, the tracking system may track the position of each of the imaging units. This greatly facilitates the calibrating of the image acquisition and improves the precision of the image acquisition. For example, during surgery, after taking an image of the relevant body part of the patient, the imaging device may be moved to another position (e.g. to an initial or retracted position), so as not to obstruct the operating field. The tracking system may include a position storage unit to store the last position or the last positions of the imaging device during image acquisition and to move the imaging device to this position (or to any of the stored positions) again when a further image needs to be acquired during surgery. This greatly improves the image calibration and the precision of image acquisition and reduces the overall image acquisition time and radiation dosage to which the patient is exposed.

The tracking system for tracking the position of the imaging device or at least components thereof (such as sensors, cabling, controlling) may be housed within the side rail or other parts of the surgical table (such as imaging device support, platform support and/or base).

Further, there may be provided a tracking system to track the position of the patient or a part of the patient's body that is imaged with respect to the base and/or with respect to the imaging device.

The surgical table may further comprise a controller for controlling the movement of the imaging device support and/or sections thereof, and/or for controlling the movement of the patient support platform in a vertical and/or horizontal direction, etc. The controller may for example further act as a human-machine connector enabling 3D Eye Tracking Software allowing surgeon's eye gaze tracking. As described above, at least a part of the controller's component(s) (such as electrical cabling, electrical component(s), sensor(s) and/or actuator(s)) may be housed within the (hollow) component(s) of the surgical table, such as base, platform supports, side rails and/or imaging device support.

The surgical table or parts thereof (e.g. the patient support platform) may be formed from carbon fiber or other suitable material that is transparent to the employed radiation.

According to another aspect, there is provided a method for obtaining images of a patient's body part comprising:
 providing a surgical table according to any one of the described aspects of the invention,
 positioning a patient on an upper surface of the patient support platform of the surgical table;
 moving the imaging device with respect to the patient support platform to an image acquiring position and obtaining at least one image of patient's body part by the imaging device.

The moving of the imaging device support may for example comprise a sliding movement and/or a rotational movement of one or more imaging units with respect to the patient support platform and/or the base, as described above in more detail. In particular, the obtaining of the least one image of patient's body part by the imaging device may comprise the above described rotational scan of the imaging device, thereby obtaining a plurality of images of the patient's body part from different direction. The rotational scan may be performed by rotating the at least one imaging unit, as described above in connection with the surgical table.

The surgical table and method according to aspects of the present invention may be employed in various types of surgical operations, in particular for performing complex surgical procedures, such as spinal surgery, neurosurgery, brain surgery, orthopedic surgery, reduced invasiveness procedures, implant device placement, traumatology, oto Rhino laryngology surgery, sinus surgery, maxilo facial surgery, plastic surgery, dentistry, biopsy, etc.

The above and other objects, features and/or advantages of the present invention will become apparent from the following description in conjunction with the accompanying drawings. It should be understood that even though embodiments are separately described, single features thereof may be combined to additional embodiments.

FIGS. 3A to 3C are different views of an exemplary surgical table with a plurality of platform sections, wherein FIG. 3A is a front view, FIG. 3B is a side view and FIG. 3C is a view from the top;

FIGS. 5A to 5C are different views of an exemplary surgical table with a plurality of platform sections, wherein FIG. 5A is a front view, FIG. 5B is a view from the top and FIG. 5C is a side view;

Figure 1:
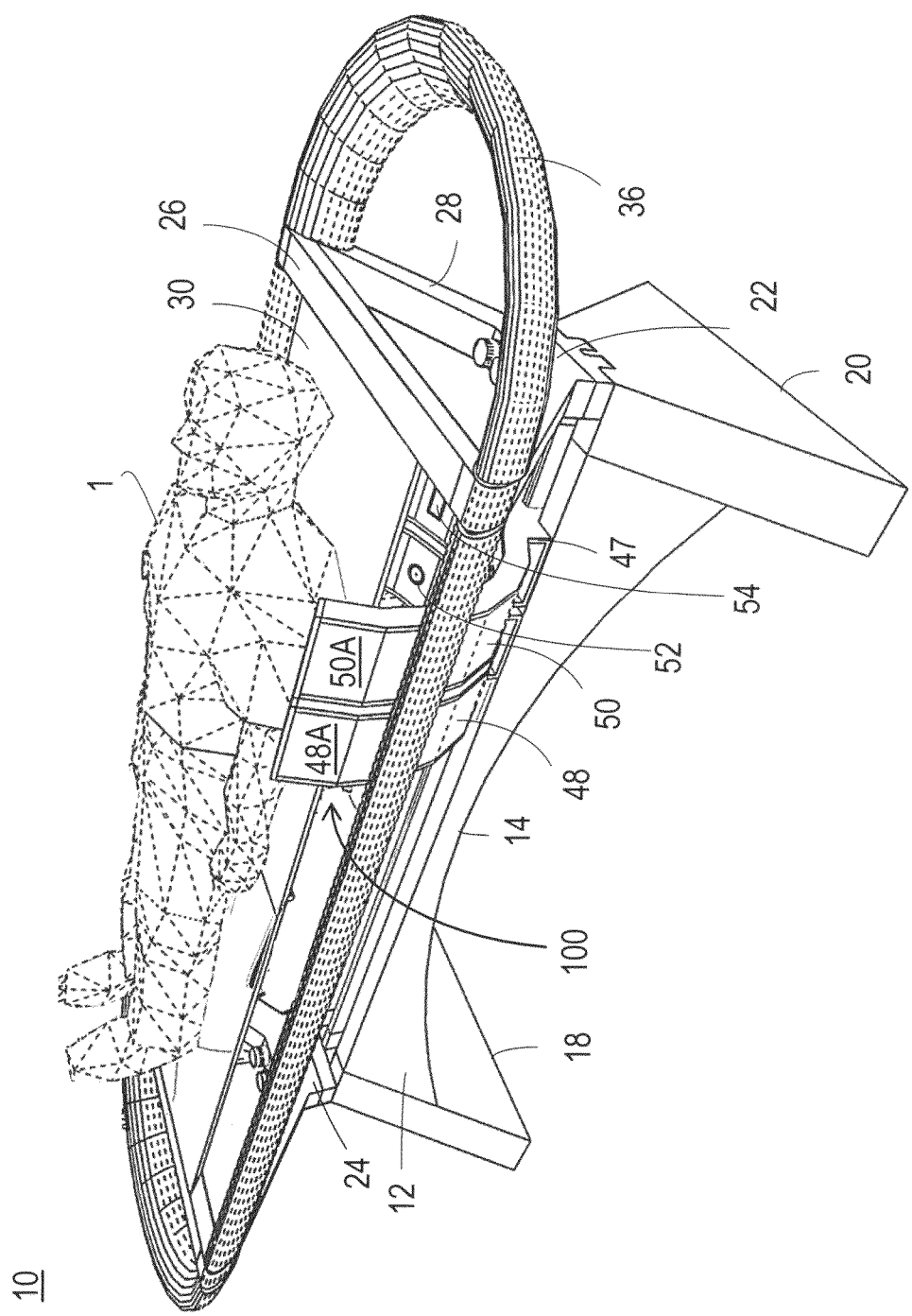
FIG. 1 is a perspective view of an exemplary surgical table with a patient placed on it.

A number of examples are described below more fully with reference to the accompanying drawings. The invention may, however, be embodied in many different forms and should not be construed as limited to the examples set forth herein. Further, even though examples are separately described, single features thereof may be combined to additional examples.

In the drawings, the size and relative sizes of elements and regions may be not up to scale and may for example be exaggerated for clarity. Like numbers refer to like elements throughout.

Further, when an element is referred to as being "on", "connected to", "coupled to" or "mounted on" another element, the element can be directly on, connected or coupled to or mounted on another element by an intervening element (such as a coupling element). In contrast, when an element is referred to as being "directly on," "directly connected to", "directly coupled to" or "directly mounted on" another element, there are no intervening elements present. As used herein, the term "and/or" includes any and all combinations of one or more of the associated listed items.

Spatially relative terms, such as "below", "lower", "under," "above", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures.

Further, although the terms first, second, third, etc., may be used herein to describe various elements, components, regions, and/or sections, these elements, components, regions and/or sections should not be limited by these terms. These terms are only used to distinguish one element, component, region or section from another element, component, region or section, respectively.

Figure 2A:
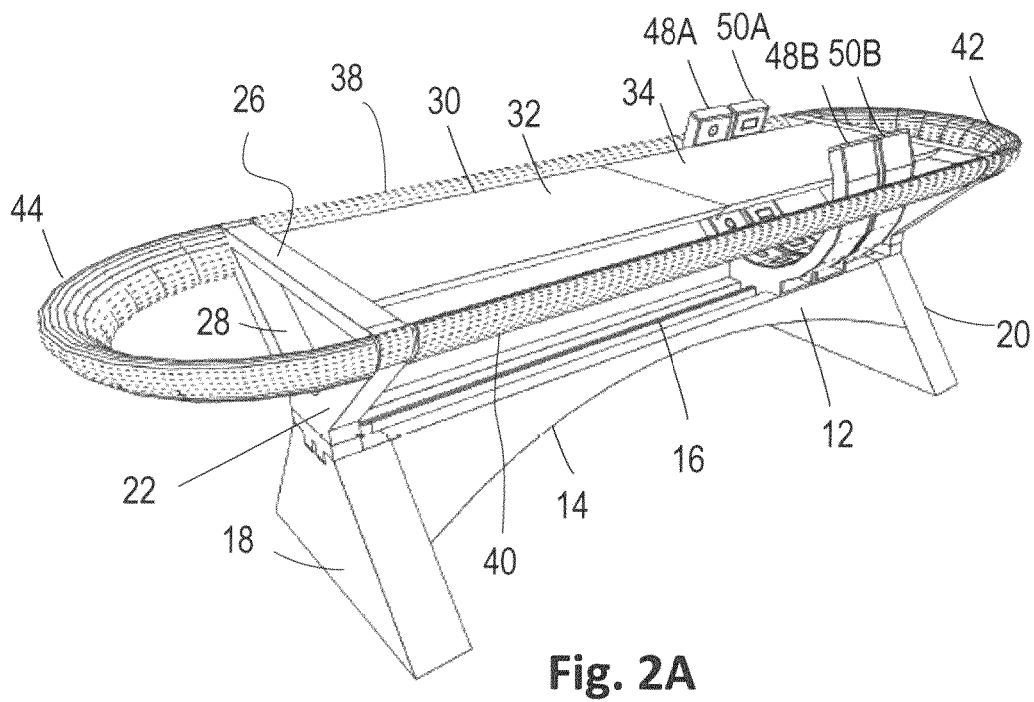
FIGS. 2A to 2C are perspective views of an exemplary surgical table with a plurality of platform sections.
Figure 2B:
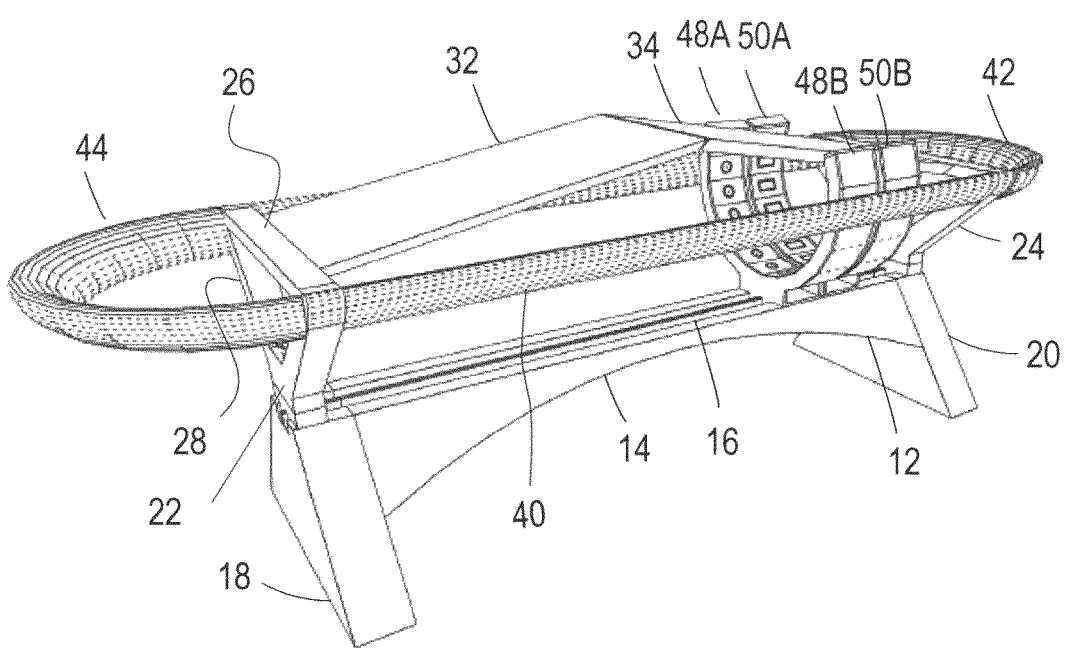
Figure 2C:
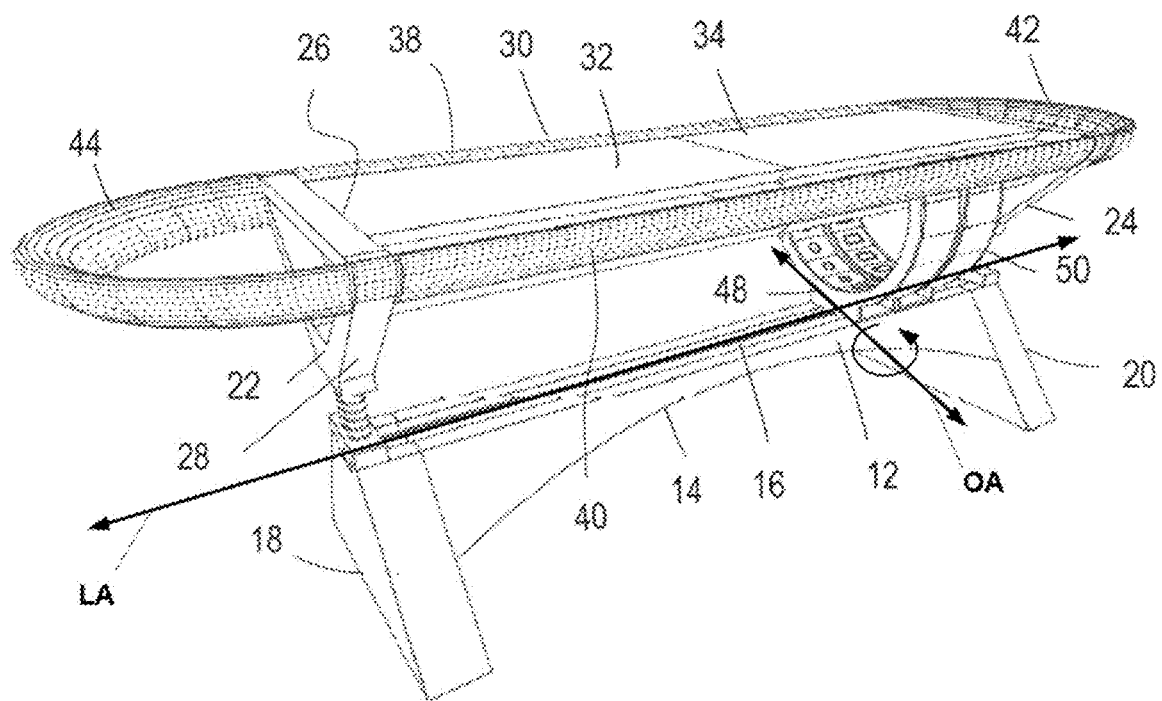
Figure 4:
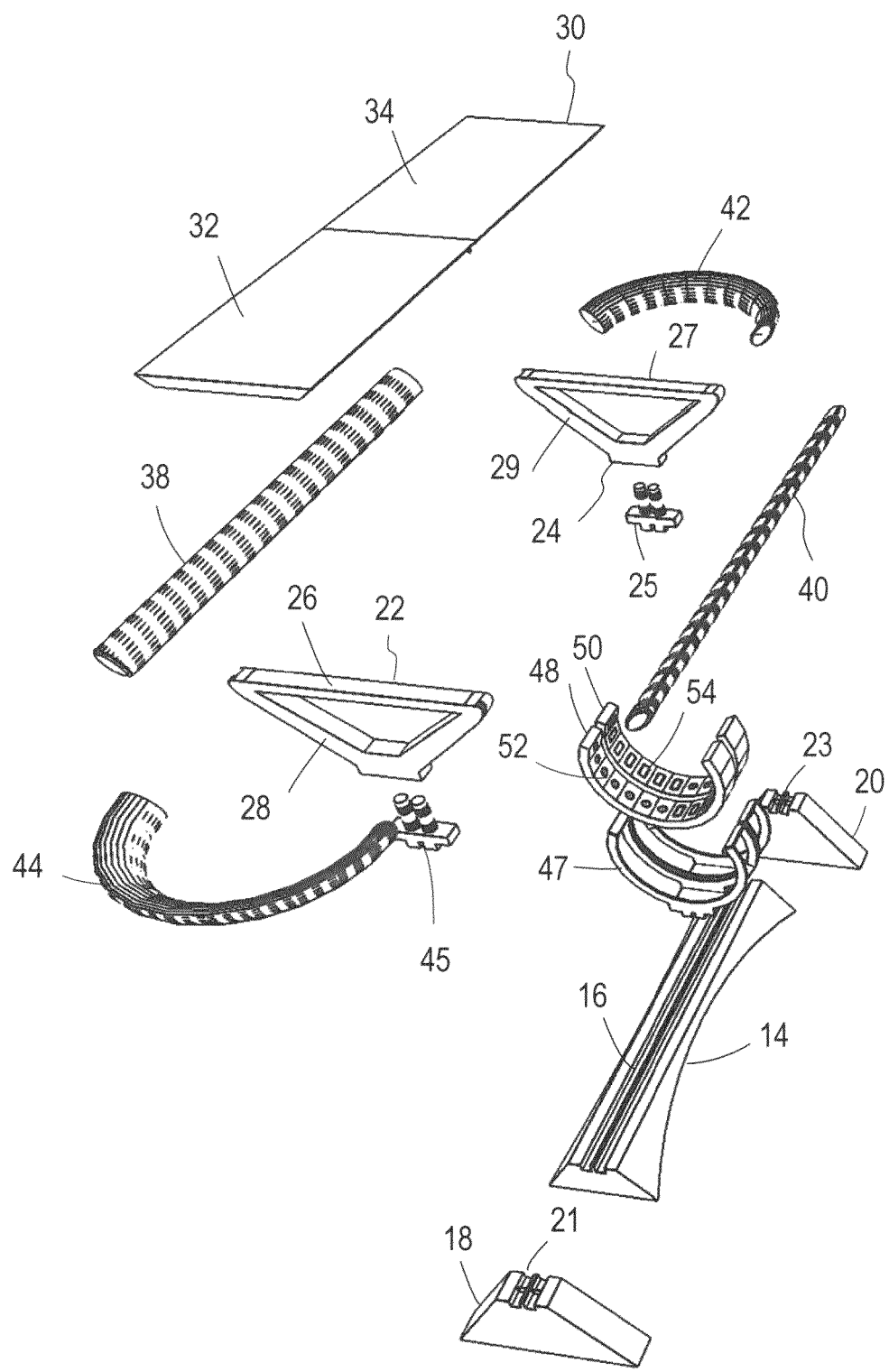
FIG. 4 is an exploded view of the parts constituting an exemplary surgical table.
Figure 5A:
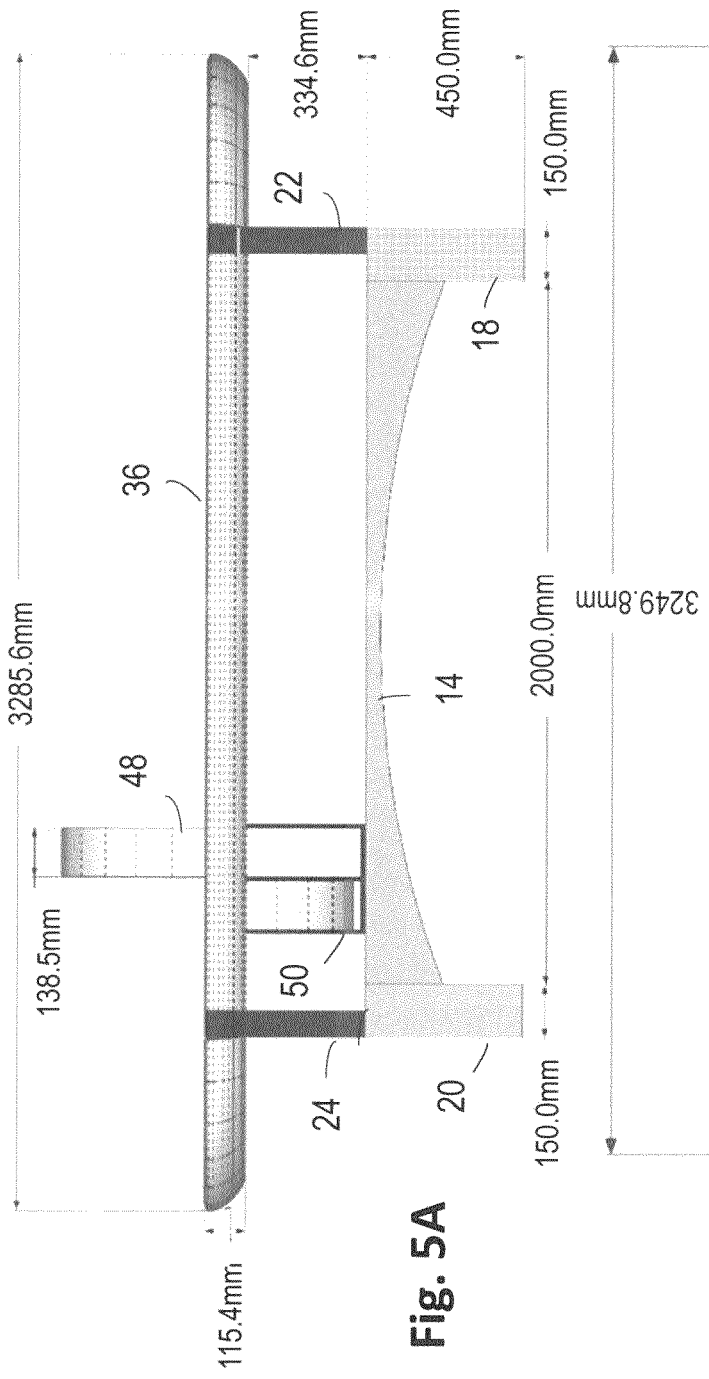
Figure 5B:
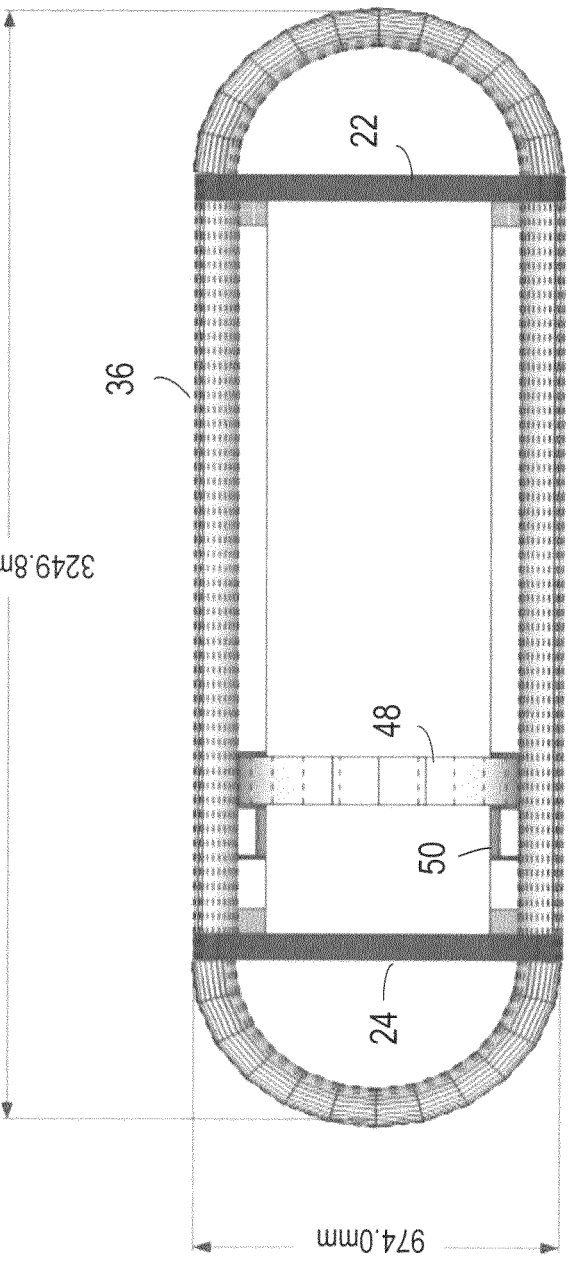
Figure 5C:
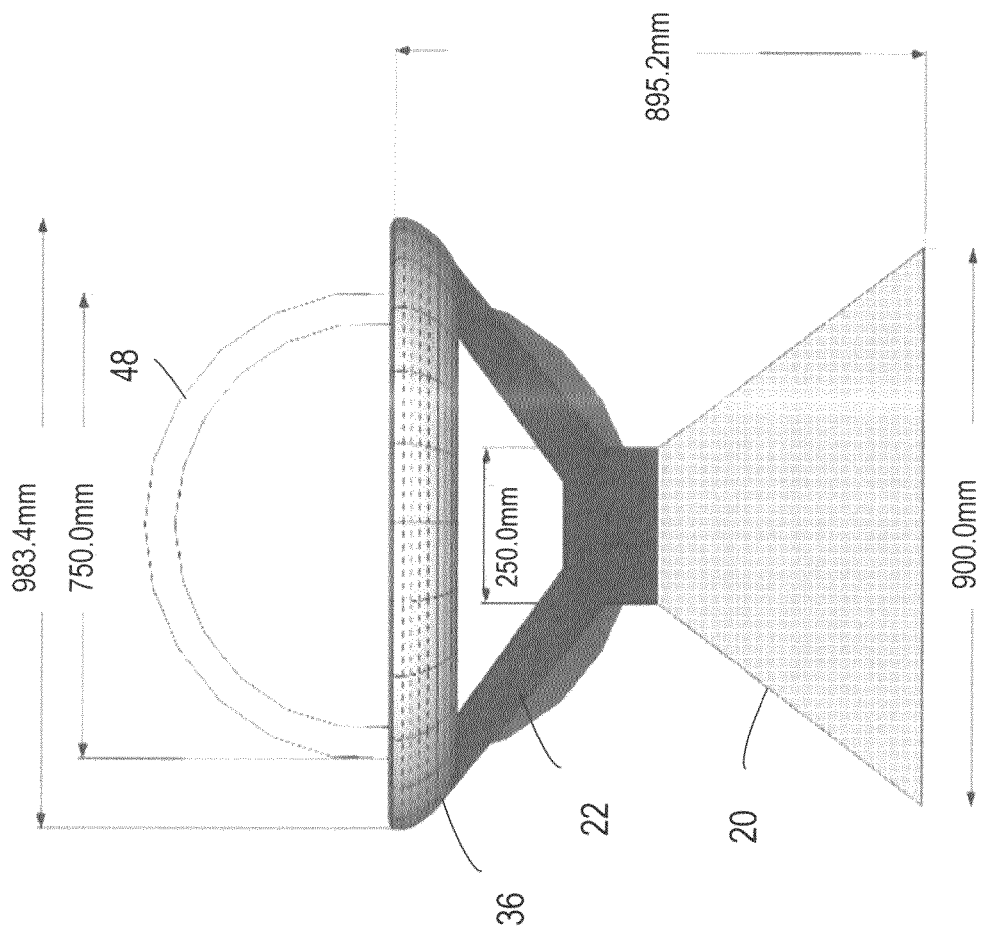
Figure 6:
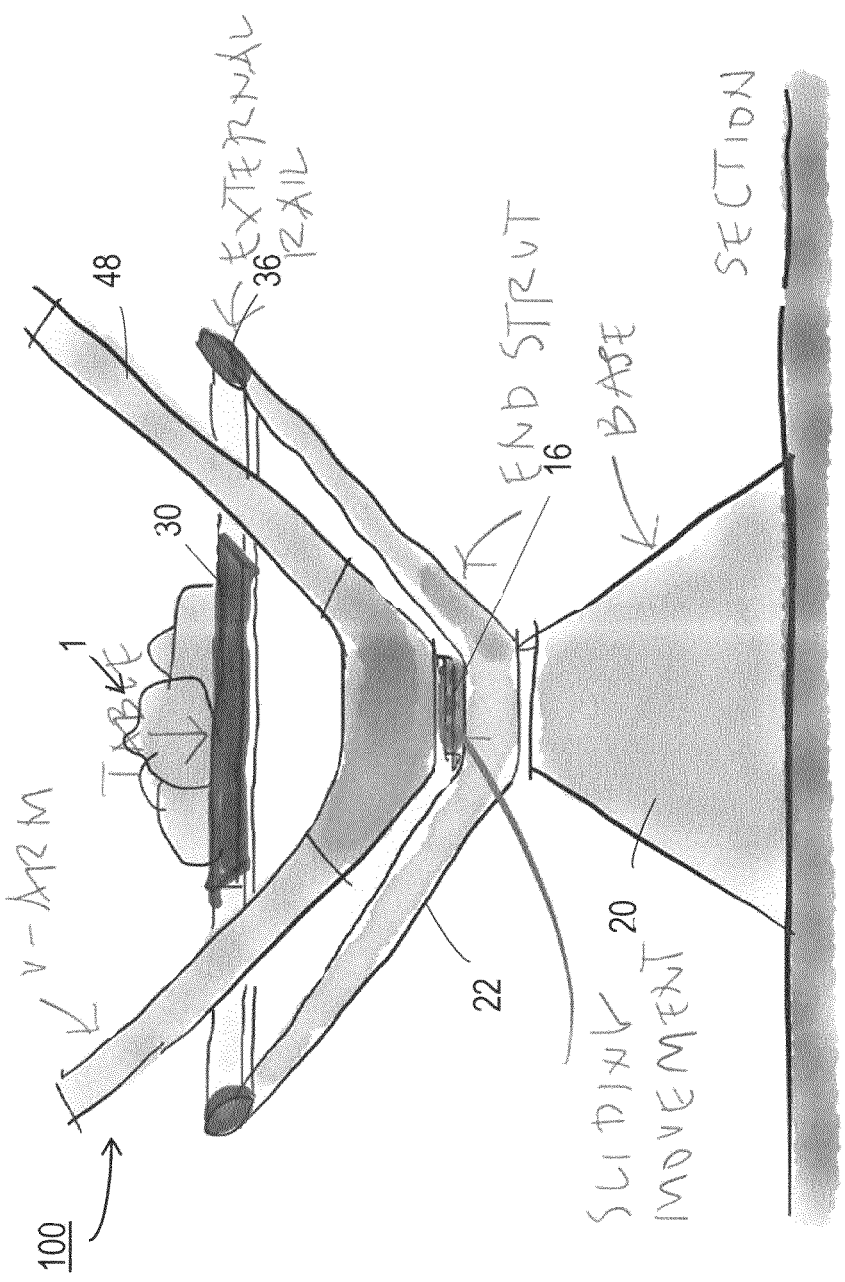
FIG. 6 is a front view of an exemplary surgical table with a V-shaped imaging unit.

FIG. 1 shows a perspective view of an exemplary surgical table 10 with a patient 1 placed on it. FIGS. 2A to 2C show different perspective views of the exemplary surgical table 10. FIGS. 3A to 3C are different views of an exemplary surgical table 10 with a plurality of platform sections, wherein FIG. 3A is a front view, FIG. 3B is a side view and FIG. 3C is a view from the top. FIG. 4 is an exploded view of the parts constituting an exemplary surgical table 10. FIGS. 5A to 5C are different views of an exemplary surgical table with additional dimensional information, wherein FIG. 5A is a front view, FIG. 5B is a view from the top and FIG. 5C is a side view FIG. 6 shows an exemplary surgical table 10 with a V-shaped imaging unit 48.

The surgical table 10 has an elongated form having a longitudinal axis LA extending in a length direction of the surgical table and a transverse axis orthogonal OA to the longitudinal axis. The surgical table 10 comprises a base 12 that can be placed on the floor of an operating room. The base 12 comprises an elongated bridge portion 14 extending in a longitudinal direction of the surgical table 10. The bridge portion is provided with a sliding rail or track 16 on its top surface facing a patient support platform 30. The sliding rail or track 16 extends in a longitudinal direction of the bridge portion 14 and respectively the longitudinal direction of the surgical table 10. The base 12 comprises further two end struts 18 und 20 positioned on both sides of the bridge portion 14, respectively. The two end struts 18 und 20 particularly have a substantially trapezoidal form, with a wider lower end of each strut being placed on the floor and a narrower upper end being connected to the respective platform support 22, 24. The bridge portion 14 and/or the end struts 18, 20 may house at least one actuator and/or other moving parts. Further, under floor lighting may be provided in the bridge portion 14 and/or the end struts 18, 20. The length of the bridge portion may be for example in the range of 1950.0 mm and 2250.0 mm, for example 2000 mm. The height of the bridge portion (which is equal to the height of the base) may be in the range of 250.0 mm and 550.0 mm, for example 450.0 mm. The width of the lower end of each of the two end struts 18 und 20 in the longitudinal direction may be within the range of 80.0 mm and 160.0 mm, for example 150.0 mm. The width of the lower end of each of the two end struts 18 und 20 in the transverse direction orthogonal to the longitudinal direction may be within the range of 600.0 mm and 800.0 mm, for example 700.0 mm. The width of the upper end of each of the two end struts 18 and 20 in the transverse direction may be within the range of 250.0 mm and 350.0 mm, for example 275.0 mm.

Two platform supports 22 and 24 are connected to the end struts 18 and 20, respectively. The connection may be via a suitable connecting mechanism. The connecting mechanism may for example comprise connecting elements 21 and 23 provided on each of the end struts 18 and 20, respectively and mating connecting elements 25, 45 that may be a part of the platform supports. Each platform support 22, 24 has a supporting bar (cross bar) 26, 27, respectively, that is connected to the patient support platform 30 and to a side rail 36 surrounding the patient support platform 30. Each platform support 22, 24 comprises further a V-form or U-form supporting strut 28, 29 having two supporting arms, the upper ends of which are connected to the ends of the supporting bars 26, 27 respectively. The lower end of the V-form or U-form supporting strut is connected to the end struts 18 and 20 of the base 12, respectively, for example via a suitable connecting mechanism.

The lower end of the V-form or U-form supporting strut may have a width in a transverse direction in the range of 250.0 mm and 350.0 mm, for example 275.0 mm. The opening angle of the V-form or U-form supporting strut may be within 35° and 70°. The height of the supporting strut may be within 600.0 mm and 750.0 mm, for example 625.0 mm.

The overall height of the surgical table 10 may for example be up to 1400.0 mm, for example 895.2 mm. Preferably, the connecting mechanism is configured to enable a change of the height of the patient support platform 30, i.e. to lift and lower the patient support platform 30, thus improving the ergonomics of the surgery table. In other words, the connecting mechanism may comprise a height adjustment mechanism. In an example, the height may of the patient support platform be altered continuously or stepwise within the range of 0800.0 mm to 1300.0 mm. Various height adjustment mechanisms are possible. For example, the height adjustment mechanism may comprise a telescopically extendable and retractable support column.

The surgical table 10 may further comprise at least one actuator (e.g. a linear actuator) that causes the vertical movement of patient support platform 30. For example, the actuator may cause a support column to extend or collapse in a vertical direction. A pair of actuators may for example be housed within the base 12, for example within the end struts 18 and 20, within the at least one platform support 22, 24 or within an extendable support column connected to the struts 18, 20. This arrangement offers considerable advantages in terms of sterility as explained above. Further, it saves space, thereby providing a compact and easy to handle surgical table.

In addition, the above described triangulated cantilever design of the surgical table 10 maintains a low centre of gravity, while at the same time facilitating the access to the patient 1. Thus, the overall surgical time and the associated risks may be reduced. Still further, the risk of sterility violation may be reduced.

The surgical table 10 comprises further a patient support platform 30 having an elongated form in the longitudinal direction of the surgical table 10, for example an oval or a rectangular form. A patient 1 may be positioned on the upper surface of the patient support platform 30. The patient 1 may be secured to the patient support platform 30 by a belt, a strap or any other suitable devices. The length of the patient support platform may for example be about 2130.0 mm. The width of the patient support platform may for example be about 550.0 mm.

The patient support platform 30 may be a multi-sectional patient support platform comprising a plurality of sections that are movable with respect to each other, as shown for example in FIGS. 1 to 4. In the examples shown in FIGS. 1 to 4, the patient support platform 30 comprises two sections 32 and 34 that are movable with respect to each other, so that the patient support platform 30 may be bent, as shown for example in FIG. 2B. The first patient support platform section 32 and the second patient platform section 34 may for example be cantilevered with respect to each other or in other words, may be connected to each other by a suitable hinge joint. Further, the two portions may be connected to platform supports 22 and 24, wherein the connection may be via a suitable hinge joint that enables the pivotable movement of the platform sections 32 and 34 with respect to the platform supports, respectively.

The multi-sectional arrangement of the surgical table 10 facilitates the correct positioning and repositioning of the patient 1 during the surgery. Of course, the patient support platform may comprise more than two sections movable with respect to each other. It is also possible that the patient support platform 30 has only one section, as shown for example in FIGS. 5A to 5C.

The patient support platform 30 is surrounded by a side rail (external rail) 36. In the examples shown in the figures the side rail 36 has an elongated oval form. The side rail 36 also surrounds imaging units 48, 50 of an imaging device 100. In other words, the imaging units 48, 50 may be within the perimeter of the side rail 36. The side rail 36 thus reduces the risk of interference of the surgeon and the supporting staff with the imaging device 100.

The length of the side rail 36 may be within the range of 2700.0 mm and 3500.0 mm b, for example 3249.8 mm. The width of the side rail 36 may be within the range of 650.0 mm and 1100.0 mm, for example 974.0 mm. At least a portion of the side rail 36 may be padded with or may be made of a soft material to prevent injuries of the operating personnel.

The side rail 36 comprises two perimeter rail portions or perimeter beams 38 and 40 on the two long sides of the patient support platform 30 and two end rail portions 42 and 44 on the short sides of the patient support platform 30, respectively. The perimeter rail portions 38 and 40 may be substantially straight or slightly curved portions. The imaging units 48 and 50 may be arranged between the perimeter rail portions 38 and 40.

The distance between the perimeter rail portions 38 and 40 and the respective long sides of the patient support platform 30 may be uniform and may be for example in the range of 125.0 mm and 250.0 mm, for example 160.0 mm. The end rail portions 42, 44 may be curved and may have for example a semi-circular or semi-oval form. The maximal distance between the perimeter rail portions end rail portions 42 and 44 and the respective short sides of the patient support platform 30 may be for example in the range of 250.0 mm and 600.0 mm, for example 450.0 mm.

The opposing ends of the supporting bars 26 of the platform supports 22 and 24 are connected to the side rail 36. According to such a structure, an increased overall stability of the surgical table 10 is achieved and/or a reliable relative positioning of the patient 1 on the patient support platform 30 with respect to the imaging system 100 can be achieved, thus yielding more accurate imaging (specifically in case of cross sectional imaging like sonography, computer tomography (CT), magnetic resonance tomography (MRT)) and 2D or 3D fluoroscopy. The perimeter rails portions 38, 40 and/or the end rail portions 42, 44 may be substantially tubular with circular or oval cross-section. Other cross-sectional forms are of course possible. The height of the side rail 36 may be within the range of 40.0 mm and 150.0 mm, for example 75.0 mm.

The side rail 36 may be further provided with a mounting track (an instrument placement portion) on or in which surgical equipment and accessories may be mounted or placed and preferably securely held or fixed thereon/therein. For example, the perimeter rail portions 38 and 40 may be extruded profiles that act as a conduit and a mounting track (instrument placement portion) for accessories and equipment (such as a display screen to fix closed to the surgical field). In an example, the mounting track may be provided in a part of the side rail 36 (for example in a part of one or more of the perimeter rail portions 38, 40 and/or the end rail portions 42, 44). The dimensions of the instrument placement portion may vary, depending on the targeted use of the surgical table.

Further, cables (e.g. neuromonitoring cables) may be accessible through the mounting track. The cables may be integer with the mounting track.

Figure 8:
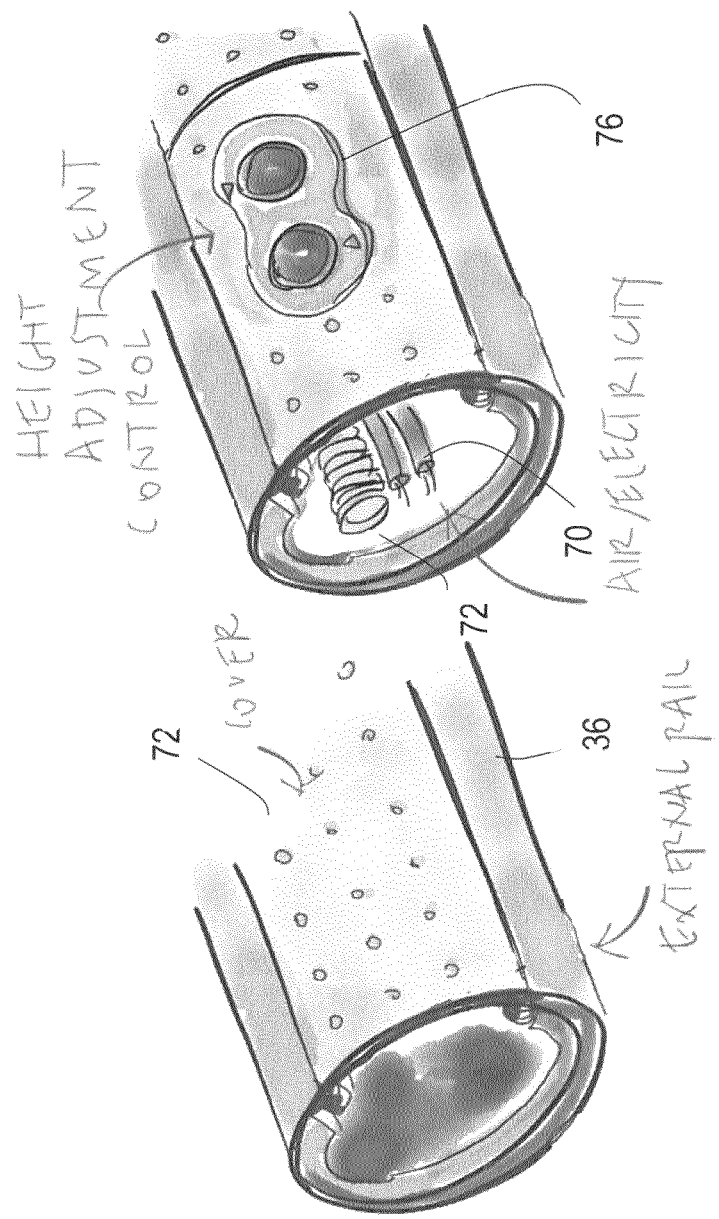
FIG. 8 is a perspective view showing a portion of a sliding rail.

Exemplary instrument placement portion is shown in FIG. 8. The instrument placement portion may for example be formed by or comprise a cover 72 covering a part of the side rail 36 in a circumferential direction thereof. The cover 72 comprises a plurality of apertures that are configured to accept respective bolts or other connecting elements of external devices (for example surgical appliances, etc.). Of course, the cover 72 may comprise other types of connecting elements or sections, such as for example rails, buttons, fasteners, etc.

By the provision of a mounting track, the ergonomics of the surgical table may be improved, resulting in reduction of the overall surgery time.

Figure 9:
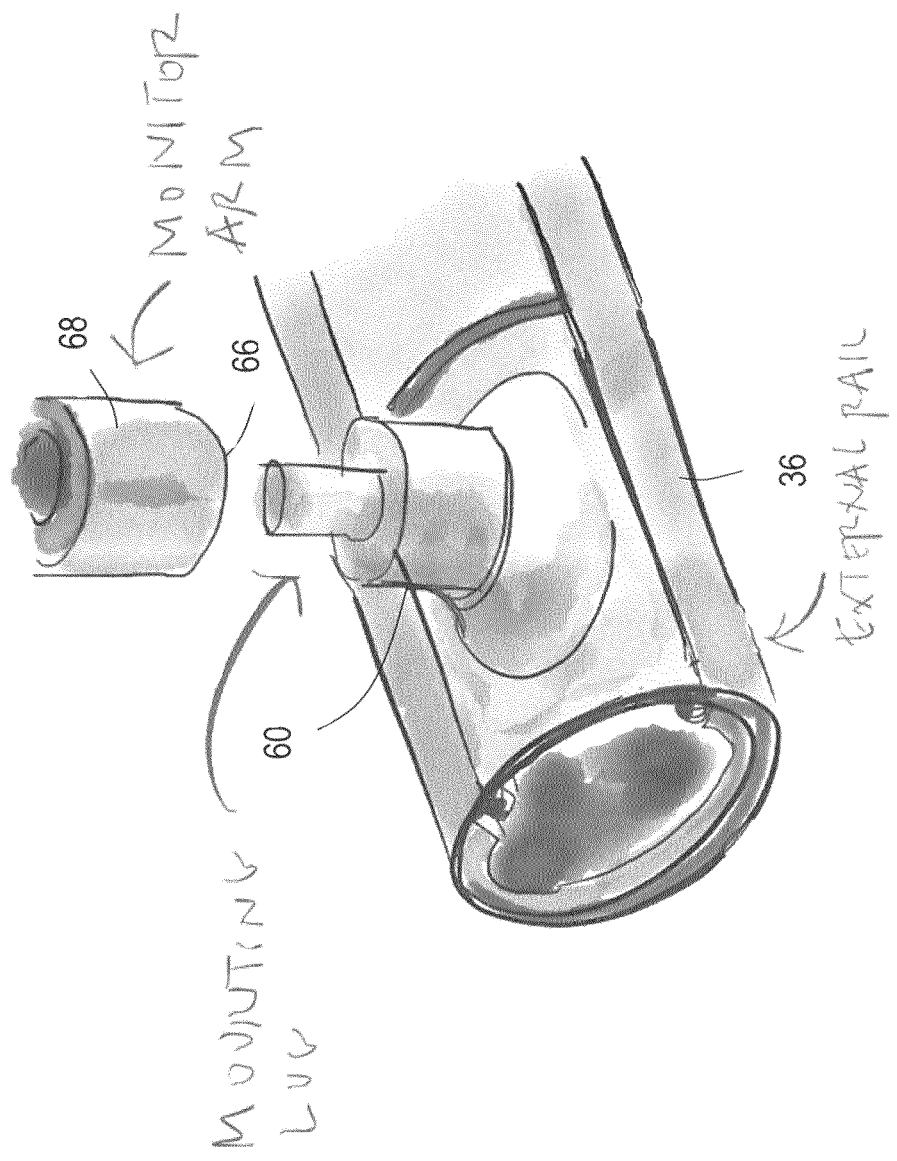
FIG. 9 is a perspective view showing a portion of a sliding rail provided with a mounting portion.
Figure 10:
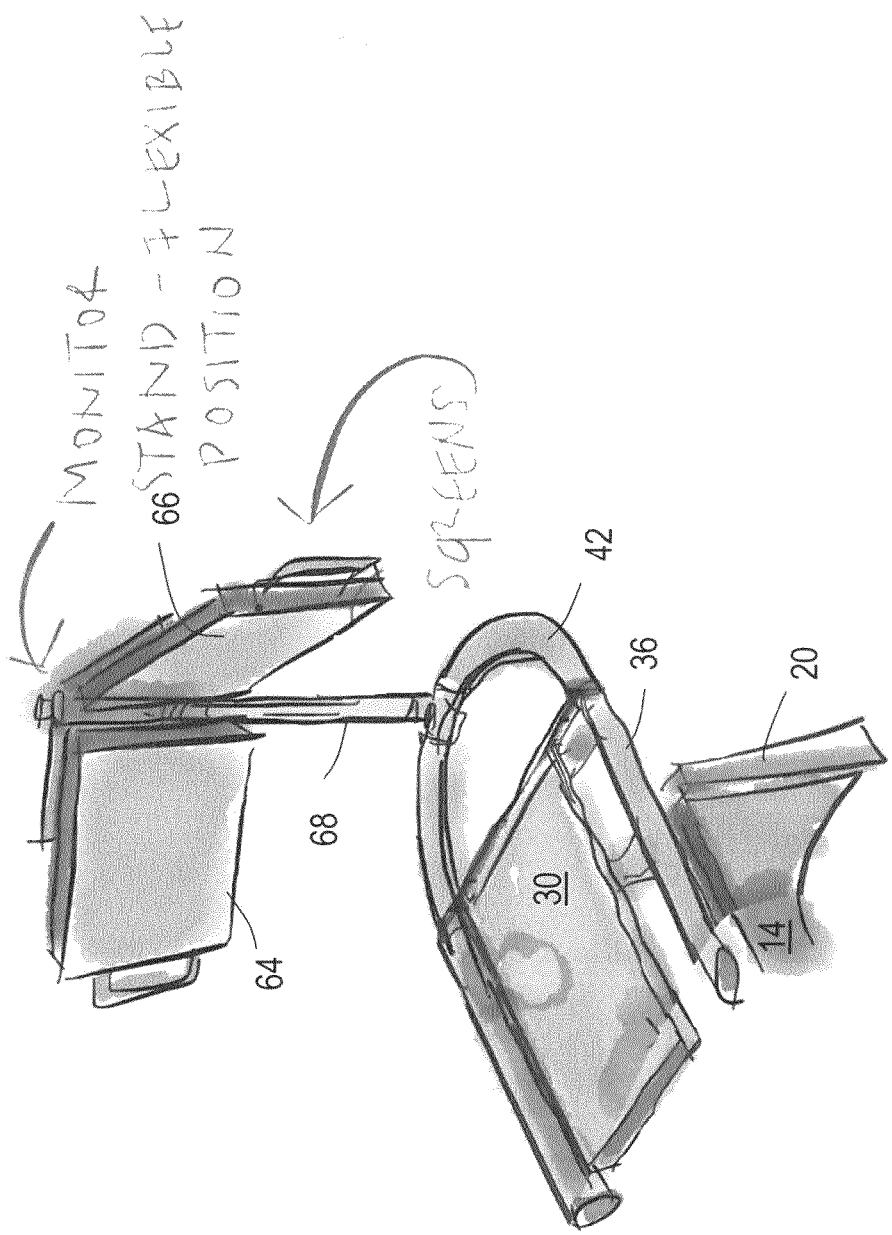
FIG. 10 is a perspective view showing a portion of the sliding rail with an external device mounted thereon.

The side rail 36 may be provided with one or more mounting portions, connectable to respective mounting portions of additional external devices, such as for example a monitor, a touchscreen, etc. Exemplary side rail 36 provided with a mounting portion is shown in FIG. 9. FIG. 10 shows a perspective view of a sliding rail with an external device mounted thereon. For example, the at least one mounting portion 62 may be provided on one or both of the semi-circular or semi-oval end rail portions 42 and 44. The mounting portion 62 of the rail portion 36 may for example comprise a mounting leg on which a mounting arm 68 of an external device support 68 (e.g. a monitor stand) is mountable. Any other type of connectors may be employed. As shown in FIG. 10, two monitors or displays 64 and 66 may be mounted on or supported by the mounting stand 68. In an example, the mounting position of the mounting stand 68 may be flexible or in other words variable. For example, the connection between the mounting stand 68 and the side rail 36 may be such as to enable moving the mounting stand to a new position along the side rail 36. The displays 64 or 66 may display an image or a plurality of acquired images by one or more of the imaging units 48, 50 and/or further information, such as surgery navigation information, information regarding vital parameters of the patient (heartrate, blood pressure, oxygen saturation, etc.). This arrangement makes is easier for the surgeon to rapidly grasp the necessary information without substantially obscuring the operation field.

Still further, in an example shown in FIG. 8, the side rail 36 or a part thereof (for example one of the perimeter portions 38, 40 and/or one of the end rail portions 42, 44) may have a hollow, substantially cylindrical form. Various components, such as electrical cabling 70, at least one fluid conduit or tube (for example for the passage of air or other fluids for an hydraulic height adjusting mechanism), electrical components (e.g. of a height adjustment control mechanism and/or or a control mechanism for moving the imaging device 100) and/or other components may be provided within the hollow side rail 36 of a part thereof. In other words, the side rail 36 or a part thereof may house any of the above mentioned components. This has considerable advantages in terms of sterility (ease of sterilizing the surgical table and/or maintaining sterile condition). Further, the maintenance of the surgical table may be improved the and the risk of obstructions of surgical field reduced.

The surgery table 10 comprises an imaging device 100 formed integrally with the surgery table 10. The imaging device 100 may be any suitable imaging device, for example a radiographic imaging device, a magnetic resonance imaging device, a positron emission imaging device, an ultrasound imaging device, a computer tomography imaging device, etc. and any combination thereof. The imaging device 100 comprises or is constituted by at least one radiation source (for example an x-ray source) and at least one radiation detector (for example an x-ray detector). In the examples shown in the figures, the radiation source comprises a plurality of source elements arranged in a one-dimensional or a two-dimensional array 52. The radiation detector comprises a plurality of detector elements arranged in a one-dimensional or a two-dimensional array 54.

The imaging device 100 is supported by an imaging device support 47 on the base 12, which is movable with respect to the base 12 and the patient support platform 30.

The imaging device 100 comprises one or more (particularly two or three) imaging units 48, 50. Each imaging unit comprises a pair of arms 48A and 48B or 50A and 50B, respectively, connected at a connection portion particularly arranged at the bottom and/or mounted on or to the base 12 to be supported by the base 12. The imaging device 100 with the imaging units 48, 50 is thus "suspended" from the base 12. Each imaging unit 48, 50 substantially has an overall geometry substantially having an open-ended C-like or V-like form (particularly substantially semi-circular or oval form). Particularly, each imaging unit 48, 50 has an azimuthal extension in a range of about 180° to about 270°, further particularly in a range of about 200° to about 250°, still further particularly an azimuthal extension of about 220°.

The two arms 48A, 48B or 50A, 50B of each imaging unit 48, 50 are arranged on or near the two long sides of the patient support platform 30. The patient support platform 30 at least partly is, thus, positioned between the arms 50A, 50B of each imaging unit 48, 50. Further, the imaging units 48, 50 are positioned within the perimeter of the side rail 36, for example between the perimeter side rail portions 38 and 40. The two imaging units 48, 50 may be positioned adjacent to each other. The relative distance between the two imaging units 48, 50 may be fixed or changeable. The plural imaging units 48, 50 may be jointly or independently displaced along the sliding rail or track 16.

One of the arms of each imaging unit 48, 50 carries the at least one radiation source and the other arm of the imaging unit the at least one radiation detector. More specifically, the one or more radiation source elements are arranged on or in or at the inner surface (i.e. the surface substantially facing the patient support platform 30) of one of the arms 48A, 58B, particularly in form of a one-dimensional or a two-dimensional array 52, 54 substantially extending at along the length of the arm. The radiation detector elements are arranged on the inner surface of the other one of the arms 48BA, 50A of the respective imaging unit 48, 50 particularly in form of a one-dimensional or a two-dimensional array substantially extending along the length of the arm.

If for example, the two arms 48A and 48B or 50A and 50B of an imaging unit 48, 50 substantially form a continuous semi-circular (C-like) form, one half of the semi-circular form may carry the array 52 of radiation source elements and the other half the array 54 of radiation detectors. It is not necessary that the radiation detector elements or radiation source elements extend along the full length of the respective arm 50A, 50B, they may be provided only in a part or parts of the respective arm(s) 50A, 50B.

In the examples shown in the figures, there are two sets of radiation source elements and radiation detector elements, each set being provided on a different one of the imaging units 48 and 50, respectively. In the examples shown in the figures, the array of radiation source elements of one of the sets provided on the first imaging unit 48 is arranged next to or adjacent the array of detector elements of the second set provided on the second imaging unit 50, as shown in FIG. 4. Other arrangements are also possible.

Each imaging unit 48, 50 is rotatable (for example around about 360 degrees or less) with respect to the base 12 and the patient support platform 30 and more specifically with respect to a longitudinal axis of the surgical table 10, thus allowing images of the patient 1 to be taken from multiple directions and/or in multiple sectional views.

Each imaging unit 48, 50 may be selectively positioned in one or more positions.

Specifically, each imaging unit 48, 50 may be position in a retracted or standby position, specifically when no image acquisition needs to be performed. In the retracted or standby position, the height of the upper ends of the arms 48A, 48B, 50A, 50B of each imaging unit 48, 50 extending above the upper surface of the patient support platform 30 may be for example within about 300 mm (the patient support platform width is set minimal) and about 525.5 mm, for example less than about 450.0 mm, so as not to substantially impede the surgical team and/or the support staff (e.g. when placing the patient 1 on the surgical table 10).

Preferably, when in retracted or standby position, the upper ends of the arms 50A, 50B of each imaging unit not extend higher than the upper surface of the patient support platform (see e.g. FIG. 2C).

The geometry and/or arrangement of the imaging units (such as for example the height of the upper ends of the arms in retracted or standby position) may be determined based on various constraints and/or requirements, such as ergonomic requirements and geometric requirements/constraints of the imaging device (such as for example radiology geometry design requirements), expected imaging quality threshold, etc.

Figure 7:
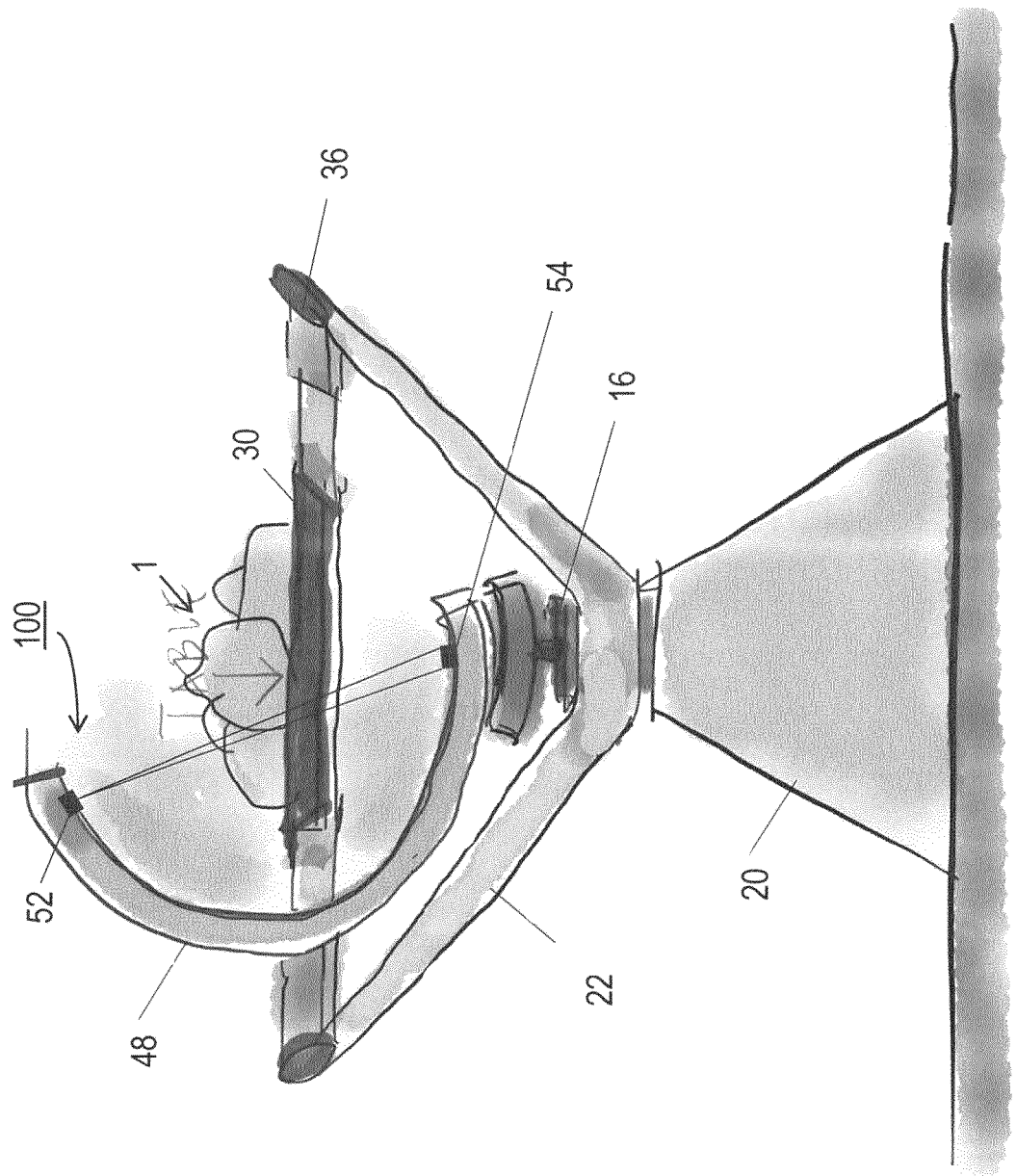
FIG. 7 illustrates schematically an image acquisition by using an exemplary surgical table.

Each imaging 48, 50 may be further position in one or more detection positions, in which images of a relevant part of the patient's body may be acquired. As illustrated in FIG. 7, in detection position at least a part of the radiation emitted from the radiation source 52 may propagate through the patient's body and be detected by the radiation detector 54. In other words, in a detection position at least a part of the patient's body that is to be imaged is arranged between the radiation source 52 and the radiation detector 54. As explained above, there may be a plurality of detection positions corresponding to different directions from which images of the body part to be imaged is taken.

The imaging unit 48, 50 may be moved to the detected position by rotating or pivoting or swivelling it around the longitudinal axis with respect to the base 12 and/or the patient support platform 30 so as to be positioned in a different azimuthal position around the longitudinal axis e.g. with respect to the retracted or standby position.

When for example, an imaging unit 48, 50 is rotated to a position above the patient support platform 30, the maximal distance between the apex or top of the imaging unit to the patient support platform 30 (e.g. in a fully closed position of a C-arm around the patient, as shown in FIG. 5C) may be for example in the range of about 350.0 (the patient support platform's width is set to be minimal) to about 750.0 mm, for example about 502.5 mm. In case of circular C shape the distance may be about 600.0 mm and 1050.0 mm (due to width 550.0 mm of table 30).

The maximal distance between the two arms 48A and 48B or 50A and 50B of the imaging unit 48 or 50, respectively (measured in a transversal direction orthogonal to the longitudinal direction of the surgical table 10) may be in the range of about 500 mm to about 1500 mm, further particularly about 600 mm to 1050 mm, still further particularly for example about 750 mm.—In case the arms 50A, 50B form a substantially continuous semi-circular form, the radius of the semi-circular form may be for example in the range of about 400.0 mm to about 750 mm, more specifically in the range of about 400.0 mm to about 502.5 mm, for example about 450 mm. The width of each arm 50A and 50B (measured in a longitudinal direction) may be in the range of about 60.0 mm to about 400.0 mm, more specifically about 150 mm to about 250 mm, for example 183.5 mm.

The geometry and/or arrangement of each of the imaging units may be set based on various constraints and/or requirements, such as ergonomic requirements and geometric requirements/constraints of the imaging device (such as for example radiology geometry design requirements), expected imaging quality threshold, etc.

The two imaging units 48, 50 may be independently movable, for example may be independently rotatable around the longitudinal axis of the surgical table 10 and/or may be independently displaceable along the sliding rail or track 16.

In the example shown in FIGS. 5A to 5C, one of the imaging units, namely imaging unit 48 is rotated with respect to the other 50 imaging unit and with respect to the longitudinal axis of the surgical table 10 (and thus also with respect to the longitudinal axis of the patient support platform 30 and the base 12). The imaging units 48, 50 may also be pivotable with respect the base 12 and/or with respect to each other. For example, the imaging units 48, 50 may be pivotable with respect to an axis that is orthogonal to the longitudinal axis of the surgical table 10 (and thus also with respect to longitudinal axis of the base 12 and the patient support platform 30). See, for example, FIG. 2C with an arrow showing a pivotal direction about the orthogonal axis OA. This may further facilitate the access to the patient and allow images of the patient to be taken from different directions.

According to a particular embodiment, the imaging 48, 50 are mounted on a support frame 47 (as an example of an imaging device support). Instead of support frame 47, any other suitable coupling mechanism may be employed. The support frame 47 is slidably mounted on or to the base 12 particularly via a sliding rail or track 16, thus facilitating the access to the patient 1 and/or allowing images of different parts of the patient 1 to be taken. In particular, as explained above, the imaging device 100 with the imaging units 48 and 50 may be moved in the longitudinal direction to a first position (detection position) at which at least one image of a relevant part of the patient's body may be obtained (for example by performing rotation scan) and a standby or retracted position (for example at or near the ends of the patient support platform 30) or any other position that does not interfere with the operating field. Before moving the support frame 47 and the imaging device 100 mounted thereon, the last detection position or positions of the support frame 47 and/or imaging device 100 may be memorized. When needed the support frame 47 and the imaging device 100 may be automatically moved to the memorized position or to one of the memorized positions. This greatly reduces the time needed for the repositioning and/or calibrating of the imaging device 100 and increases the precision of the image acquisition. The position of the support frame 47 and/or imaging device 100 with respect to the base 12 and/or the patient support platform 30 may be tracked by a suitable tracking system, for example an optical or electronical tracking system. The tracking system or at least parts thereof may be integrated within the side rail 36. As shown for example in FIG. 8, the side rail 36 may be provided with at least one control interface (for example in form of buttons, touch screen, etc.) to control the movement of the support frame 47 and/or the imaging device 100.

The support frame 47 carries the imaging units 48, 50, while allowing rotation of the imaging units 48, 50 with respect to the longitudinal axis of the surgical table 10, so that a rotation scan can be performed.

In the examples shown in the figures, the base 12 comprises a sliding rail or track 16 that substantially extends along a longitudinal axis of the base 12 (particularly corresponding to a longitudinal axis of the patient support platform 30). The imaging device 100 and more specifically the imaging units 48, 50 is/are slidably mounted on the sliding rail or track 16 via the support frame 47 or any other suitable coupling mechanism. Further, different support frames may be provided for each imaging unit 48, 50, thereby enabling independent sliding movement of each imaging unit 48, 50.

The surgical table 10 may further comprise at least one actuator (e.g. a linear actuator) for moving the imaging device support 47 with respect to the base 12 and/or for rotatably and/or pivotably moving the imaging units 48, 50 of the imaging device 100. The at least one actuator may be housed in the base 12 (for example in the bridge portion 14).

As described above, the surgical table 10 may further comprise a tracking system (e.g. optical, electronical, etc. tracking system) for tracking the position of the imaging device support 47 and/or the imaging device 100 (particularly composed of the radiation source and radiation detector) with respect to the base 12. This facilitates the calibrating of the image acquisition. Alternatively or additionally, there may be provided a tracking system to track the position of the patient 1 or a part of the patient's body that is imaged with respect to the base 12 and/or with respect to the imaging device 100.

A method for obtaining images of a patient's body part with the above described surgical table 10 may comprise positioning the patient 1 on the upper surface of the patient support platform 30 and moving the imaging device support 47 with respect to the patient support platform 30 to an image acquiring position. The moving of the imaging device support 47 may for example comprise a sliding movement and/or a rotational movement of one or more imaging units 48, 50 with respect to the patient support platform 30. In the image acquiring position, the patient 1 at least partly is arranged or positioned between the arms 48A and 48B and/or 50A and 50B of the imaging units 48 and/or 50, respectively, so that at least one image (specifically a sectional image) of patient's body part may be obtained by the imaging device 100 constituted by or comprising the at least one radiation source 52 (constituted for example by a one-dimensional or a two-dimensional array of radiation source elements) and the at least one radiation detector 54 (constituted for example by a one-dimensional or a two-dimensional array of radiation detector elements). As described above, by rotating the imaging units 48, 50 with respect to a longitudinal axis of the surgical table 10, a plurality of images from different directions or orientations may be obtained. The signal detected by the radiation detector 54 may be transmitted to a computer or a computing system, where it may be processed to form a two- or three-dimensional image of the patient's body part. The image may be shown on a display, for example a display that is mounted on the side rail 36, 38 and/or 40. The signal from the radiation detector 54 may also be transmitted to a navigation system that may be used to assist the surgeon during the surgery. The obtained image and optionally further information (such as navigational information, vital parameters information, etc.) may be shown on at least one or more displays, for example external displays 64 and 66 shown in FIG. 10.

The surgical table and method according described above may be employed in various types of surgical operations, in particular for performing complex surgical procedures, such as spinal surgery, neurosurgery, brain surgery, orthopedic surgery, reduced invasiveness procedures, implant device placement, traumatology, oto Rhino laryngology surgery, sinus surgery, maxilo facial surgery, plastic surgery, dentistry, biopsy, etc.

The surgical table and method according described above may have one or more of the following advantages:

Since the imaging device 100 is mounted on or in other words connected to the base 12 via the imaging device support 47, it forms an integral part of the surgical table 10 itself. Thus, the relative position of the imaging device support 47 and of the imaging device 100 with respect to the surgical table 10 can be obtained and/or maintained and in a precise manner. Further, it is possible to precisely move the imaging device 100 to a desired position with respect to the surgical table 10 and more specifically with respect to the base 12 and/or the patient support platform 30. Thus, the precision of the image acquisition may be considerably improved. Further, the process of calibration of the imaging device 100 may be considerably improved and/or the time required for the calibration procedure considerably shortened. Thus, the patient exposure time and the radiation dosage may be reduced, and the security of the surgical intervention may be improved. Further, since the access to the patient 1 is also facilitated, the overall surgical time and the associated risks may be reduced. Still further, the described surgical table 10 offers considerable advantages in terms of assuring and maintaining sterility, in particular as compared to systems, such as the system according to U.S. Pat. No. 7,188,998 B2 or US 2012/0330134 A1. Still further, since the imaging device 100 is an integral part of the surgical table 10 and is directly suspended from it, it has considerable advantages in terms of space economy. For example, no space needs to be proved for an additional, as a rule rather bulky base of an external imaging device.

The above described exemplary surgical table(s) 10 may further offer open, easy access to the surgical field as well as excellent mechanical stability. Further, robotic features (for example controllers, actuators) may be easily integrated. In some examples the surgery table 10, for example the base 12, the platform support(s) 22, 24 and/or the side rail(s) 36, 38 and/or 40, at least partly may house or in other words may have arranged within one or more control elements, one or more actuators, at least one electrical cabling, at least one (particularly fluid) tubing, sensors, and/or other elements. Since these elements are not exposed during the surgical operation, the sterility requirements may be easily met and maintained. Further, navigation and/or other user interface elements (for example control interface elements 76) may be integrated within the surgical table 12, which increases the user friendliness and/or ergonomics of the surgical table 10.

Examples of the proposed surgical table may be modular and/or easily extendible or integratable with other external devices, such as display, touch screens, control panels, etc. Further, examples of the proposed surgical table may be provided with sections that may be configured to accept and/or hold further surgical devices, such as surgical accessories, instruments, etc.

The above described exemplary surgical table(s) 10 may exhibit a simple, robust and versatile construction that can be easily maintained. Further, there may be no need to book a technical for manipulation, which reduces the costs. The proposed surgical table 10, thus, offers direct and indirect cost reduction.

A number of examples have been described above. Needless to say, the invention is not limited to these examples, but may encompass various modifications and/or combinations thereof.

LIST OF REFERENCE NUMERALS 1 patient
10 surgical table
12 base
14 bridge portion
16 sliding rail or track
18, 20 end struts
21,23 connecting element
22, 24 platform supports
25 connecting element
26,27 supporting bar 28,29 supporting strut
30 patient support platform
32 first patient support platform section
34 second patient support platform section
36 side rail
38, 40 perimeter rail portions
42, 44 end rail portions
45 connector element (coupling mechanism rail, supporting strut, end strut)
47 imaging device support
47 support frame
48 a first imaging unit
48A, 48B arm of the first imaging unit
50 a second imaging unit
50A, 50B arm of the second imaging unit
52 radiation source element array (example of a radiation source)
54 radiation detector element array (example of a radiation detector)
60 mounting portion of the side rail (e.g. mounting leg)
62 mounting portion of an external device (e.g. mounting arm)
64, 66 external device (e.g. display, touch screen)
68 external device support (e.g. a monitor stand)
70 electrical cabling
72 fluid conduits or tubing
74 cover
76 control interface (e.g. height adjustment control interface)
100 imaging device

The invention claimed is:

1. A surgical table comprising:
a base;
a patient support platform;
at least one platform support connected to the base and configured to support the patient support platform on the base;
an imaging device support that is mounted on the base;
an imaging device mounted on the imaging device support, said imaging device including:
a plurality of imaging units comprising a first arm and a second arm, wherein the patient support platform is at least partly positioned between the first arm and the second arm of respective ones of the plurality of imaging units, wherein one arm of each imaging unit is provided with a first radiation source and the other arm of the imaging unit is provided with a first radiation detector arranged to detect at least a portion of the radiation emitted from a respective corresponding radiation source,
wherein the imaging units are movable with respect to each other, and/or with respect to the base and/or the patient support platform, and
wherein, when in an imaging orientation, at least one imaging unit of the plurality of imaging units is pivotable with respect to an axis orthogonal to a longitudinal axis of the surgical table via a hinge connection.

2. The surgical table of claim 1, wherein the imaging device support is slidably mounted on the base.

3. The surgical table of claim 1, wherein at least one imaging unit of the plurality of imaging units is rotatable with respect to a longitudinal axis of the surgical table.

4. The surgical table of claim 1, wherein the arms of at least one imaging unit of the plurality of imaging units are arranged so as to jointly substantially have a c-form or a v-form; and/or
wherein the second arm of at least one imaging unit of the plurality of imaging units includes a second radiation source and the first arm of the at least one imaging unit includes a second radiation detector arranged such as to detect at least a portion of the radiation emitted from the second radiation source.

5. The surgical table of claim 1, wherein the patient support platform is movable in a vertical direction with respect to the base.

6. The surgical table of claim 1, wherein the surgical table or parts thereof are formed from carbon fiber.

7. The surgical table of claim 1, wherein the base comprises:
a bridge portion provided with a sliding rail or track particularly on its top surface, the sliding rail or track substantially extending in a longitudinal direction of the bridge portion; and
two end struts positioned on the bridge portion particularly at or near opposite distal ends thereof, said two end struts having optionally a trapezoidal form, wherein a lower end is placeable on a floor and an upper end being connected to the platform support.

8. The surgical table of claim 1, wherein the platform support comprises;
a supporting bar that is connected to the patient support platform and optionally to a side rail surrounding the patient support platform; and
a V-form or U-form supporting strut having two supporting arms, the upper ends of which are connected to the ends of the supporting bar, respectively.

9. The surgical table of claim 1, wherein the patient support platform comprises a plurality of sections that are pivotable with respect to each other.

10. The surgical table of claim 9, wherein the patient support platform comprises a first section and a second section cantilevered off or hinged on the first section.

11. The surgical table of claim 1, further comprising a side rail at least partially surrounding an outer circumference of the patient support platform.

12. The surgical table of claim 11, wherein the side rail comprises one or more mounting portions connectable to respective mounting portions of additional external devices and/or an instrument placement portion on which surgical equipment and accessories are placeable.

13. The surgical table of claim 11, wherein the side rail has a hollow tubular cross-sectional form housing at least one of electrical cabling, fluid conduits or electrical components.

14. The surgical table of claim 1, further comprising:
a tracking system configured to track the position of the imaging device support and/or the imaging device with respect to the base and/or the patient support platform.

15. The surgical table of claim 1, further comprising:
a tracking system configured to track the position of the patient or a part of the patient's body that is imaged with respect to the base and/or with respect to the imaging device.

16. A method for obtaining images of a patient's body part comprising:
providing the surgical table of claim 1,
positioning a patient on an upper surface of the patient support platform;
moving the imaging device with respect to the patient support platform to an image acquiring position; and
obtaining at least one image of patient's body part by the imaging device.

17. A surgical table comprising:
a base;
a patient support platform;
at least one platform support connected to the base and configured to support the patient support platform on the base;
an imaging device support that is mounted on the base;
an imaging device mounted on the imaging device support, said imaging device including:
- at least one imaging unit comprising a first arm and a second arm, wherein the patient support platform is at least partly positioned between the first arm and the second arm, and
- a plurality of radiation sources and a plurality of radiation detectors, the plurality of radiation sources and the plurality of radiation detectors comprising:
  - a first radiation source positioned in or on the first arm and a first radiation detector positioned in or on the second arm; and
  - a second radiation source positioned in or on the first arm or the second arm and a second radiation detector positioned in or on the second arm or the first arm, the second radiation detector arranged such as to detect at least a portion of the radiation emitted from the second radiation source,
wherein the plurality of radiation sources and the plurality of radiation detectors are arranged in a stationary geometry,
wherein the plurality of radiation sources and the plurality of radiation detectors are arranged in a one-dimensional or two-dimensional array, and
wherein the plurality of radiation sources and the plurality of radiation detectors are arranged in an alternating pattern.

18. The surgical table of claim 17, wherein the plurality of radiation sources and the plurality of radiation detectors are controllable and activatable in conjunction.

* * * * *

UNITED STATES PATENT AND TRADEMARK OFFICE
CERTIFICATE OF CORRECTION

PATENT NO. : 12,357,248 B2
APPLICATION NO. : 17/435828
DATED : July 15, 2025
INVENTOR(S) : Boscherini et al.

Page 1 of 1

It is certified that error appears in the above-identified patent and that said Letters Patent is hereby corrected as shown below:

In the Claims

Column 22, Lines 12-17, Claim 7 "The surgical table of claim 1, wherein the base comprises: a bridge portion provided with a sliding rail or track particularly onits top surface, the sliding rail or track substantially extending in a longitudinal direction of the bridge portion; and" should read -- The surgical table of claim 1, wherein the base comprises: a bridge portion provided with a sliding rail or track particularly on its top surface, the sliding rail or track substantially extending in a longitudinal direction of the bridge portion; and --

Signed and Sealed this
Twenty-eighth Day of October, 2025

John A. Squires
*Director of the United States Patent and Trademark Office*